(12) United States Patent
Otsuka

(10) Patent No.: US 10,605,714 B2
(45) Date of Patent: Mar. 31, 2020

(54) IMAGE PROCESSING DEVICE, FINE PARTICLE SORTING DEVICE, AND IMAGE PROCESSING METHOD

(71) Applicant: Sony Corporation, Tokyo (JP)

(72) Inventor: Fumitaka Otsuka, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/767,426

(22) PCT Filed: Jul. 15, 2016

(86) PCT No.: PCT/JP2016/070938
§ 371 (c)(1),
(2) Date: Apr. 11, 2018

(87) PCT Pub. No.: WO2017/068822
PCT Pub. Date: Apr. 27, 2017

(65) Prior Publication Data
US 2018/0313740 A1    Nov. 1, 2018

(30) Foreign Application Priority Data
Oct. 19, 2015   (JP) .................................. 2015-205919

(51) Int. Cl.
*G01N 15/14* (2006.01)
*G01N 15/10* (2006.01)

(52) U.S. Cl.
CPC ..... *G01N 15/1404* (2013.01); *G01N 15/1425* (2013.01); *G01N 15/1436* (2013.01);
(Continued)

(58) Field of Classification Search
CPC ........... G01N 15/1404; G01N 15/1459; G01N 15/1484; G01N 2015/1415;
(Continued)

(56) References Cited

U.S. PATENT DOCUMENTS 3,710,933 A    1/1973   Fulwyler et al.
3,826,364 A    7/1974   Bonner et al.
(Continued)

FOREIGN PATENT DOCUMENTS

CN    1950690 A    4/2007
EP    1403633 A2   3/2004
(Continued)

OTHER PUBLICATIONS

Written Opinion and English translation thereof dated Sep. 27, 2016 in connection with International Application No. PCT/JP2016/070938.
(Continued)

*Primary Examiner* — Joseph C Rodriguez
(74) *Attorney, Agent, or Firm* — Wolf, Greenfield & Sacks, P.C.

(57) ABSTRACT

Provided are: an image processing device; a fine particle sorting device; and an image processing method, in which electric charge can be easily and accurately applied to a droplet.
An image processing device including: a control unit adapted to set a light source lighting delay time to control a light source, the light source lighting delay time indicating a time from a time point when a fine particle in fluid is detected by a detection unit until a time point when the light source is turned on for the fine particle included in a droplet formed from the fluid; a processing unit adapted to identify positional information of the fine particle on the basis of an image of the fine particle acquired in accordance with lighting of the light source during the set light source lighting delay time; and a recording unit adapted to record, in a correlated manner, the positional information identified in the processing unit and the light source lighting delay time. The processing unit determines, as a drop delay time, (Continued)

a light source lighting delay time correlated to target positional information that is predetermined positional information, and the drop delay time indicates a time from the time point when the fine particle is detected by the detection unit until the droplet is formed from the fluid containing the fine particle.

11 Claims, 12 Drawing Sheets

(52) U.S. Cl.
CPC . *G01N 15/1459* (2013.01); *G01N 2015/1081* (2013.01); *G01N 2015/149* (2013.01); *G01N 2015/1477* (2013.01)

(58) Field of Classification Search
CPC ......... G01N 2015/149; B01L 3/502761; B01L 3/502784
See application file for complete search history.

(56) References Cited

U.S. PATENT DOCUMENTS

| | | | |
|---|---|---|---|
| 3,924,947 A | 12/1975 | Hogg | |
| 4,009,435 A | 2/1977 | Hogg | |
| 4,168,460 A | 9/1979 | Menke | |
| 4,173,415 A | 11/1979 | Wyatt | |
| 4,284,496 A | 8/1981 | Newton | |
| 4,318,480 A | 3/1982 | Lombardo et al. | |
| 4,318,481 A | 3/1982 | Lombardo et al. | |
| 4,325,483 A | 4/1982 | Lombardo et al. | |
| 4,538,733 A | 9/1985 | Hoffman | |
| 4,616,234 A | 10/1986 | Wint | |
| 4,987,539 A | 1/1991 | Moore et al. | |
| 5,080,770 A | 1/1992 | Culkin | |
| 5,180,065 A | 1/1993 | Touge et al. | |
| 5,483,469 A | 1/1996 | Van den Engh et al. | |
| 5,602,039 A | 2/1997 | Van den Engh | |
| 5,700,692 A | 12/1997 | Sweet | |
| 5,776,781 A | 7/1998 | Vardanega et al. | |
| 6,079,836 A | 6/2000 | Burr et al. | |
| 6,202,734 B1 | 3/2001 | Sackinger et al. | |
| 6,248,590 B1 | 6/2001 | Malachowski | |
| 6,372,506 B1 | 4/2002 | Norton | |
| 6,410,872 B2 | 6/2002 | Campbell et al. | |
| 6,589,792 B1 | 7/2003 | Malachowski | |
| 6,861,265 B1 | 3/2005 | den Engh | |
| 6,941,005 B2 | 9/2005 | Lary et al. | |
| 6,949,715 B2 | 9/2005 | Kelly | |
| 7,019,293 B1 | 3/2006 | Hamada | |
| 7,024,316 B1 | 4/2006 | Ellison et al. | |
| 7,159,752 B2 | 1/2007 | Farnworth | |
| 7,417,734 B2 | 8/2008 | Kanda | |
| 7,639,358 B2 | 12/2009 | Kanda | |
| 7,691,636 B2 | 4/2010 | Frazier et al. | |
| 7,723,116 B2 | 5/2010 | Evans et al. | |
| 7,758,811 B2 | 7/2010 | Durack et al. | |
| 7,880,108 B2 | 2/2011 | Schembri et al. | |
| 7,901,947 B2 | 3/2011 | Pollack et al. | |
| 8,246,805 B2 | 8/2012 | Shinoda | |
| 8,570,511 B2 | 10/2013 | Wang | |
| 8,681,335 B2 | 3/2014 | Sharpe et al. | |
| 8,691,584 B2 | 4/2014 | Durack et al. | |
| 8,748,183 B2 | 6/2014 | Durack et al. | |
| 8,883,513 B2 | 11/2014 | Pollack et al. | |
| 8,922,636 B1 | 12/2014 | Belden et al. | |
| 8,922,646 B2 | 12/2014 | Neckels et al. | |
| 9,029,724 B2 | 5/2015 | Hashimoto et al. | |
| 9,087,371 B2 | 7/2015 | Muraki | |
| 9,339,823 B2 | 5/2016 | Muraki et al. | |
| 9,429,276 B2 | 8/2016 | Katsumoto | |
| 9,588,036 B2 | 3/2017 | Shinoda | |
| 9,784,659 B2 | 10/2017 | Tanase et al. | |
| 9,784,660 B2 | 10/2017 | Otsuka et al. | |
| 9,857,286 B2 | 1/2018 | Muraki et al. | |
| 9,958,375 B2 | 5/2018 | Muraki et al. | |
| 9,964,968 B2 | 5/2018 | Sharpe et al. | |
| 10,126,225 B2 * | 11/2018 | Marquette | G01N 15/1404 |
| 10,132,735 B2 | 11/2018 | Muraki | |
| 10,241,025 B2 | 3/2019 | Otsuka et al. | |
| 10,309,891 B2 | 6/2019 | Muraki et al. | |
| 10,309,892 B2 | 6/2019 | Otsuka | |
| 10,386,287 B2 | 8/2019 | Otsuka et al. | |
| 2002/0171827 A1 | 11/2002 | van den Engh | |
| 2003/0222950 A1 | 12/2003 | Jeanmaire | |
| 2004/0062685 A1 | 4/2004 | Norton et al. | |
| 2004/0086159 A1 | 5/2004 | Lary et al. | |
| 2005/0030534 A1 | 2/2005 | Oldham et al. | |
| 2006/0125856 A1 | 6/2006 | Kitami et al. | |
| 2006/0177348 A1 | 8/2006 | Yasuda et al. | |
| 2007/0102634 A1 | 5/2007 | Frey et al. | |
| 2007/0195310 A1 | 8/2007 | Kanda | |
| 2007/0257215 A1 | 11/2007 | Rich | |
| 2008/0024619 A1 | 1/2008 | Ono | |
| 2008/0050283 A1 | 2/2008 | Chou et al. | |
| 2008/0053205 A1 | 3/2008 | Pollack et al. | |
| 2008/0067068 A1 | 3/2008 | Li | |
| 2008/0092655 A1 | 4/2008 | Takiguchi | |
| 2008/0255705 A1 | 10/2008 | Degeal et al. | |
| 2008/0284827 A1 | 11/2008 | Fagerquist et al. | |
| 2008/0289966 A1 | 11/2008 | Voldman et al. | |
| 2009/0125242 A1 | 5/2009 | Choi et al. | |
| 2009/0170186 A1 | 7/2009 | Wu et al. | |
| 2010/0009445 A1 | 1/2010 | Patra et al. | |
| 2010/0118300 A1 | 5/2010 | Wang et al. | |
| 2010/0297759 A1 | 11/2010 | Kanda | |
| 2010/0315639 A1 | 12/2010 | Muraki | |
| 2011/0005931 A1 | 1/2011 | Zhe et al. | |
| 2011/0033339 A1 | 2/2011 | Muraki | |
| 2011/0081684 A1 | 4/2011 | Gauer et al. | |
| 2011/0221892 A1 | 9/2011 | Neckels et al. | |
| 2011/0259749 A1 | 10/2011 | Kanda | |
| 2011/0267457 A1 | 11/2011 | Weitz et al. | |
| 2011/0275052 A1 | 11/2011 | Schenk et al. | |
| 2011/0284378 A1 | 11/2011 | Shinoda | |
| 2011/0287976 A1 | 11/2011 | Wang et al. | |
| 2012/0076349 A1 | 3/2012 | Manri et al. | |
| 2012/0084022 A1 | 4/2012 | Giovangrandi et al. | |
| 2012/0135874 A1 | 5/2012 | Wang et al. | |
| 2012/0200857 A1 | 8/2012 | Sharpe et al. | |
| 2012/0202237 A1 | 8/2012 | Sedoglavich et al. | |
| 2012/0247231 A1 | 10/2012 | Kery et al. | |
| 2012/0301869 A1 | 11/2012 | Evans | |
| 2012/0314096 A1 | 12/2012 | Kruglick | |
| 2013/0188040 A1 | 7/2013 | Kamen et al. | |
| 2013/0194589 A1 | 8/2013 | Suzuki | |
| 2013/0256136 A1 | 10/2013 | Muraki et al. | |
| 2013/0256197 A1 | 10/2013 | Katsumoto | |
| 2013/0258075 A1 | 10/2013 | Muraki et al. | |
| 2013/0286038 A1 | 10/2013 | Kamath et al. | |
| 2014/0021370 A1 | 1/2014 | Suzuki et al. | |
| 2014/0043436 A1 | 2/2014 | Bell et al. | |
| 2014/0097129 A1 | 4/2014 | Foster et al. | |
| 2014/0144817 A1 | 5/2014 | Hashimoto et al. | |
| 2014/0174206 A1 | 6/2014 | Akiyama et al. | |
| 2014/0193059 A1 | 7/2014 | Muraki | |
| 2014/0212917 A1 | 7/2014 | Durack et al. | |
| 2014/0346047 A1 | 11/2014 | Shinoda | |
| 2014/0354795 A1 | 12/2014 | Tracy et al. | |
| 2015/0068957 A1 | 3/2015 | Otsuka et al. | |
| 2015/0285726 A1 | 10/2015 | Tanase et al. | |
| 2015/0285727 A1 | 10/2015 | Muraki | |
| 2016/0148433 A1 | 5/2016 | Petrovskaya et al. | |
| 2016/0223451 A1 | 8/2016 | Muraki et al. | |
| 2016/0245736 A1 | 8/2016 | Muraki et al. | |
| 2016/0266027 A1 | 9/2016 | Muraki et al. | |
| 2017/0191925 A1 | 7/2017 | Otsuka et al. | |
| 2017/0241889 A1 | 8/2017 | Otsuka et al. | |
| 2018/0058999 A1 | 3/2018 | Otsuka et al. | |
| 2018/0188150 A1 | 7/2018 | Muraki et al. | |
| 2019/0219494 A1 | 7/2019 | Otsuka et al. | |

(56) References Cited

U.S. PATENT DOCUMENTS

| | | |
|---|---|---|
| 2019/0271633 A1 | 9/2019 | Otsuka et al. |
| 2019/0301994 A1 | 10/2019 | Suzuki et al. |
| 2019/0323945 A1 | 10/2019 | Otsuka et al. |

FOREIGN PATENT DOCUMENTS

| | | |
|---|---|---|
| EP | 1 757 922 A1 | 2/2007 |
| EP | 1 916 519 A2 | 4/2008 |
| EP | 2 397 836 A1 | 12/2011 |
| EP | 2 400 286 A1 | 12/2011 |
| GB | 1 103 190 A | 2/1968 |
| JP | 53-013263 | 2/1978 |
| JP | 56-030870 A | 3/1981 |
| JP | 58-187441 U1 | 12/1983 |
| JP | 62-036542 A | 2/1987 |
| JP | 62-167478 A | 7/1987 |
| JP | 64-012245 A | 1/1989 |
| JP | 09-189653 A | 7/1997 |
| JP | H09-196855 A | 7/1997 |
| JP | 10-507525 A | 7/1998 |
| JP | 11-501258 A | 2/1999 |
| JP | 2002-505423 A | 2/2002 |
| JP | 2002-521658 A | 7/2002 |
| JP | 2004-257756 A | 9/2004 |
| JP | 2005-315799 A | 11/2005 |
| JP | 2006-504970 A | 2/2006 |
| JP | 2006-242849 A | 9/2006 |
| JP | 2006-292769 A | 10/2006 |
| JP | 2007-532874 A | 11/2007 |
| JP | 2008-107110 A | 5/2008 |
| JP | 2009-145213 A | 7/2009 |
| JP | 2009-198511 A | 9/2009 |
| JP | 2009-541093 A | 11/2009 |
| JP | 2009-298012 A | 12/2009 |
| JP | 2010-510782 A | 4/2010 |
| JP | 2010-190680 A | 9/2010 |
| JP | 2010-216992 A | 9/2010 |
| JP | 2010-286292 A | 12/2010 |
| JP | 2010-286341 A | 12/2010 |
| JP | 2011-033598 A | 2/2011 |
| JP | 4805417 B1 | 2/2011 |
| JP | 2011-509075 A | 3/2011 |
| JP | 2011-232033 A | 11/2011 |
| JP | 2011-237201 A | 11/2011 |
| JP | 2012-047464 A | 3/2012 |
| JP | 2013-210264 A | 10/2013 |
| JP | 2013-210270 A | 10/2013 |
| JP | 2015-152439 A | 8/2015 |
| WO | WO 1996/012172 A1 | 4/1996 |
| WO | WO 1999/044037 A1 | 9/1999 |
| WO | WO 2000/005566 A1 | 2/2000 |
| WO | WO 2001/002836 A1 | 1/2001 |
| WO | WO 2004/042647 A1 | 5/2004 |
| WO | WO 2010/095391 A1 | 8/2010 |
| WO | WO 2010/129787 A2 | 11/2010 |
| WO | WO 2010/140460 A1 | 12/2010 |
| WO | WO 2013/145905 A1 | 10/2013 |
| WO | WO 2014/115409 | 7/2014 |
| WO | WO 2014/115409 A1 | 7/2014 |
| WO | WO 2015/122160 A1 | 8/2015 |

OTHER PUBLICATIONS

International Preliminary Report on Patentability and English translation thereof dated May 3, 2018 in connection with International Application No. PCT/JP2016/070938.
International Search Report and Written Opinion dated Jan. 8, 2015 in connection with International Application No. PCT/JP2014/005167.
International Preliminary Report on Patentability dated Apr. 28, 2016 in connection with International Application No. PCT/JP2014/005167.
International Search Report and Written Opinion and English translation thereof dated Nov. 18, 2014 in connection with International Application No. PCT/JP2014/074610.
International Preliminary Report on Patentability and English translation thereof dated Apr. 28, 2016 in connection with International Application No. PCT/JP2014/074610.
International Search Report and English translation thereof dated Sep. 27, 2016 in connection with International Application No. PCT/JP2016/070938.
International Search Report and Written Opinion dated Nov. 6, 2015 in connection with International Application No. PCT/JP2015/004282.
International Preliminary Report on Patentability dated Mar. 16, 2017 in connection with International Application No. PCT/JP2015/004282.
International Search Report and Written Opinion and English translation thereof dated Feb. 24, 2015 in connection with International Application No. PCT/JP2014/080588.
Japanese Office Action and English translation thereof dated Dec. 15, 2015 in connection with Japanese Application No. 2012-080366.
Chinese Office Action and English translation thereof dated Mar. 3, 2016 in connection with Chinese Application No. 2013100954250.
International Search Report and Written Opinion dated Mar. 11, 2014 in connection with International Application No. PCT/JP2013/005910.
International Preliminary Report on Patentability dated May 21, 2015 in connection with International Application No. PCT/JP2013/005910.
Japanese Office Action dated Feb. 23, 2016 in connection with Japanese Application No. 2012-246432 and English translation thereof.
International Search Report and English translation thereof dated Mar. 12, 2013 in connection with Application No. PCT/JP2013/053324.
International Preliminary Report on Patentability and English translation thereof dated Oct. 9, 2014 in connection with Application No. PCT/JP2013/053324.
Extended European Search Report dated Aug. 26, 2014 in connection with Application No. 13768656.4.
International Search Report and Written Opinion and English translation thereof dated Mar. 5, 2013 in connection with Application No. PCT/JP2013/052467.
Japanese Office Action dated Jul. 15, 2014 and English translation thereof in connection with Application No. 2013-547043.
International Search Report and Written Opinion and English translation thereof dated Mar. 5, 2013 in connection with Application No. PCT/JP2013/051800.
International Search Report and Written Opinion and English translation thereof dated Jan. 21, 2014 in connection with Application No. PCT/JP2013/081152.
International Preliminary Report on Patentability and English translation thereof dated Oct. 9, 2014 in connection with Application No. PCT/JP2013/051800.
Chinese Office Action dated Aug. 25, 2015 in connection with Chinese Application No. 2013800154978 and English translation thereof.
Extended European Search Report dated Sep. 23, 2016 in connection with European Application No. 13872550.2.
International Preliminary Report on Patentability and English translation thereof dated Aug. 6, 2015 in connection with Application No. PCT/JP2013/081152.
International Preliminary Report on Patentability and English translation thereof dated Aug. 25, 2016 in connection with International Application No. PCT/JP2014/080588.
Bonner et al., Flourescence Activated Cell Sorting. Review of Scientific Instruments. Mar. 1972; 43(3):404-9.
McIntyre et all., Quantitative SLM-based differential interference contrast imaging. Optics Express. Jun. 2010; 18(13):14063-78.
Murphy et al., Differential Interference Contrast, Olympus Microscopy Resource Center, https://web.archive.org/web/20030312041453/http://www.olympusmicro.com:80/primer/tecniques/dic/dichome.

(56) References Cited

OTHER PUBLICATIONS html, retrieved from the WayBack Machine on Mar. 30, 2018, noting date of Mar. 12, 2003, 3 pages.

No Author Listed, The Epics® Altra™ Flow Cytometer, Sorting Tutorial, Jul. 1, 2000, Coulter International Corporation, 47 pages.

Shapiro, HM, Chapter 6: Flow Sorting, Practical Flow Cytometry, 4th Edition, Dec. 31, 2003, pp. 257-271.

Yoshimura et al., The Latest Technology [Modern Technology] of a Cell Sorter, Applied Research Report, Jasco Report. 1990;32(1):1-20.

Hartman et al., Jet break-up in electrohydrodynamic atomization in the cone-jet mode. J. Aerosol Sci. vol. 31(1), pp. 65-95; Mar. 1999.

Luo et al., Three-dimensional tracking of fluorescent particles applied to micro-fluidic measurements. 2006. J. Micromech. Microeng. vol. 16; 1689-1699.

Morton et al., Hydrodynamic metamaterials: Microfabricated arrays to steer, refract, and focus streams of biomaterials. PNAS May 27, 2008. vol. 105(21); 7434-7438.

Orme et al., Electrostatic charging and deflection of nonconventional droplet streams formed from capillary stream breakup. Phys. Fluids. vol. 12(9); Sep. 2000; pp. 2224-2235.

Yoon et al., 3D particle position and 3D velocity field measurement in microvolume via the defocusing concept. Meas. Sci. Technol. 17 (2006) 2897-2905.

Japanese Office Action dated Feb. 26, 2019 in connection with Japanese Application No. 2015-137487, and English translation thereof.

Pereira et al., Defocusing digital particle image velocimetry and the three-dimensional characterization of two-phase flows. 2002. Meas. Sci. Technol. vol. 13; pp. 683-694.

European Communication pursuant to Article 94(3) EPC dated Apr. 8, 2019 in connection with European Application No. 14 882 507.8.

European Communication pursuant to Article 94(3) EPC dated Jun. 12, 2019 in connection with European Application No. 13 872 550.2.

Japanese Office Action dated Sep. 3, 2019 in connection with Japanese Application No. 2015-137487, and English translation thereof.

* cited by examiner

FIG. 3
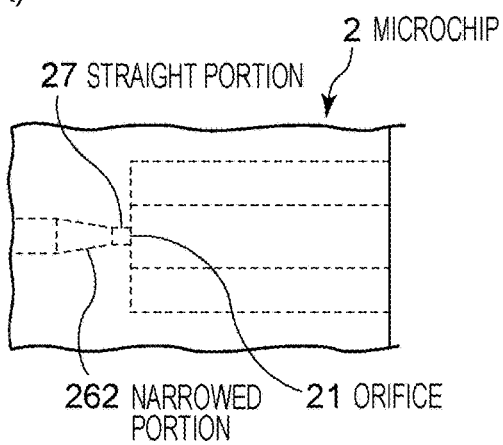
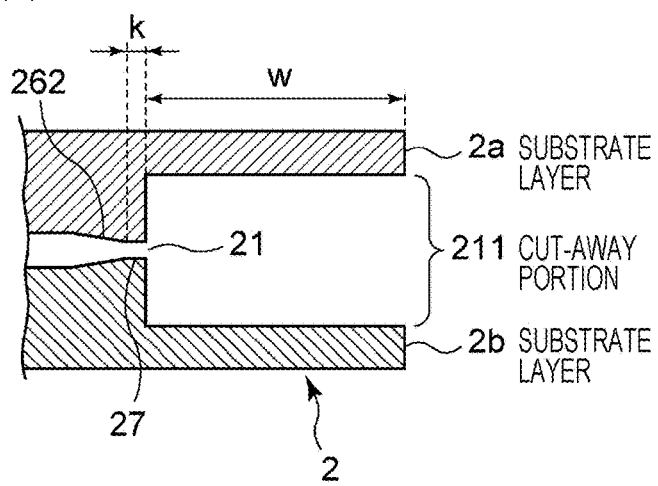
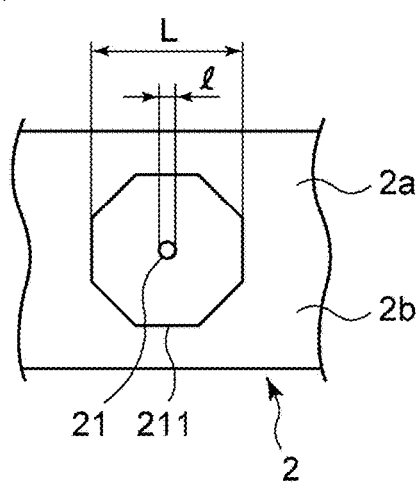

FIG. 5
(A) 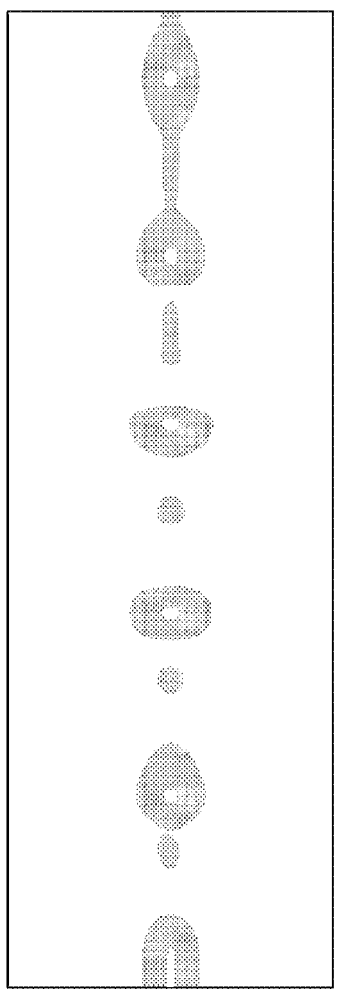
(B) 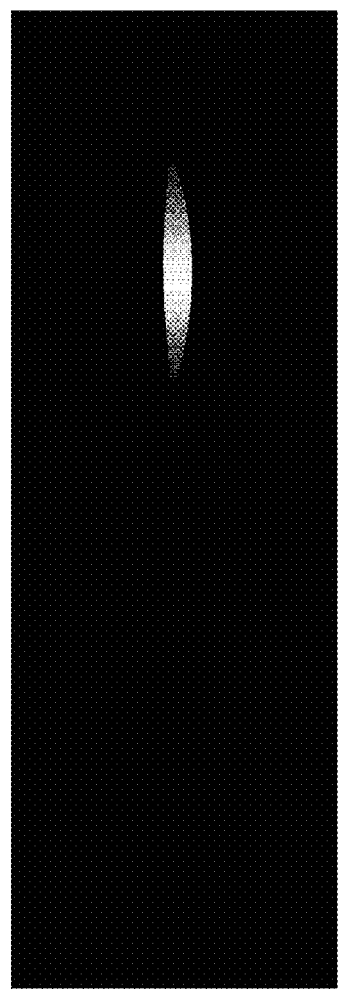
DROPLET IMAGE ACQUIRED
BY LED Strobe LIGHT SOURCE
FINE PARTICLE IMAGE ACQUIRED
BY Laser Strobe LIGHT SOURCE FIG. 6
(A)
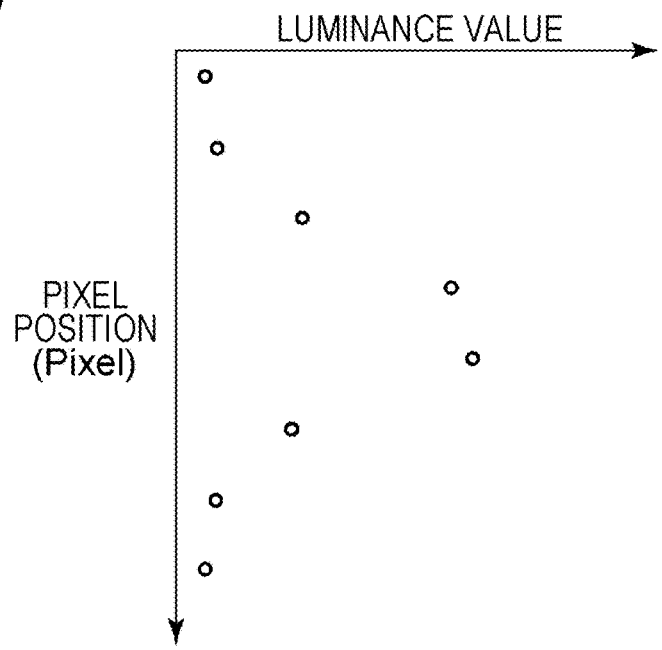
(B)
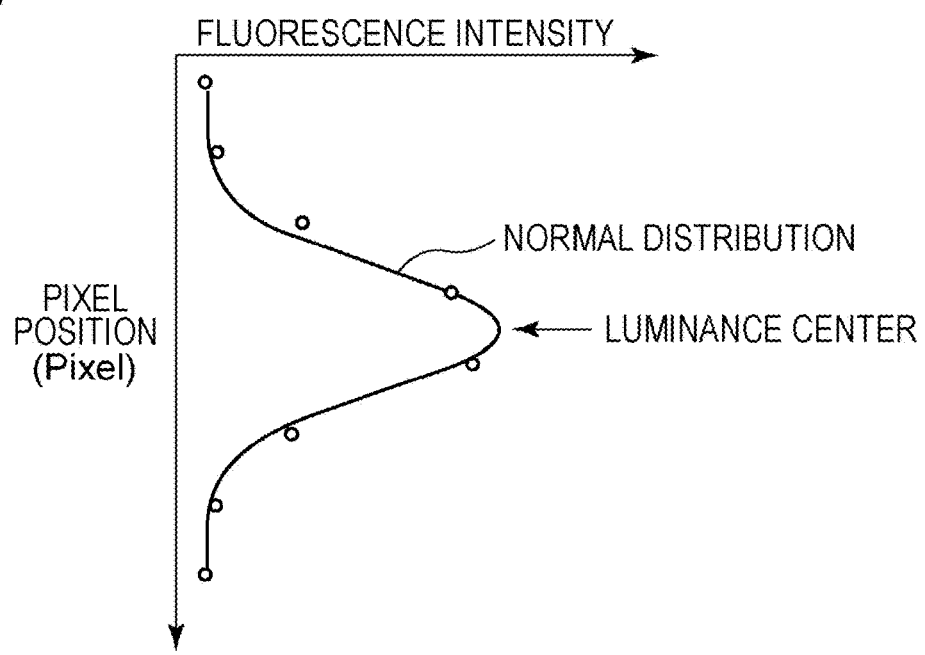

IMAGE PROCESSING DEVICE, FINE PARTICLE SORTING DEVICE, AND IMAGE PROCESSING METHOD

CROSS-REFERENCE TO RELATED APPLICATIONS

This application claims the benefit under 35 U.S.C. § 371 as a U.S. National Stage Entry of International Application No. PCT/JP2016/070938, filed in the Japanese Patent Office as a Receiving Office on Jul. 15, 2016, which claims priority to Japanese Patent Application Number JP2015-205919, filed in the Japanese Patent Office on Oct. 19, 2015, each of which applications is hereby incorporated by reference in its entirety.

TECHNICAL FIELD

The present disclosure relates to an image processing device, a fine particle sorting device, and an image processing method.

BACKGROUND ART

There is a known fine particle sorting device (e.g., flow cytometer) that optically, electrically, or magnetically detects a characteristic of a fine particle of a cell or the like, and sorts and collects only a fine particle having a predetermined characteristic.

During cell sorting by the flow cytometer, a fluid stream (laminar flow including sample liquid including a cell, and sheath liquid) is firstly generated from an orifice formed in a flow cell, vibration is applied to the orifice so as to form a droplet from the fluid stream, and electric charge is applied to the droplet. Then, a moving direction of the droplet including the cell discharged from the orifice is electrically controlled, and a target cell having a desired characteristic and a non-target cell other than the mentioned cell are collected in different collection containers.

For example, Patent Document 1 discloses, as a microchip type flow cytometer, "a fine particle sorting device including: a microchip provided with a flow path through which liquid including a fine particle is made to flow, and an orifice to eject the liquid flowing through the flow path; a vibration element to form a droplet from the liquid at the orifice and discharge the droplet; charging means to apply electric charge to the discharged droplet; optical detection means to detect an optical characteristic of a fine particle flowing through the flow path; a pair of electrodes facing each other interposing the moving droplet and disposed along a moving direction of the droplet discharged to a space outside the chip; and two or more containers to collect droplets having passed between the pair of electrodes".

Additionally, Patent Document 2 discloses a method of controlling operation of a flow cytometer capable of confirming whether a droplet is sorted to an intended flow path by arranging an auxiliary light and a detection unit at a position where the droplet breaks off from fluid. Since the break-off point is thus grasped, a delay time from when a fine particle of a cell or the like is detected until the droplet including the cell or the like reaches the break-off point can be grasped, and electric charge can be applied to the droplet containing a minute particle detected on the basis of the delay time.

CITATION LIST

Patent Document

Patent Document 1: Japanese Patent Application Laid-Open No. 2010-190680
Patent Document 2: Japanese Patent Application Laid-Open No. 2007-532874

SUMMARY OF THE INVENTION

Problems to be Solved by the Invention

However, a break-off position is varied by discharging conditions and the like of a droplet, and a delay time described above is also changed accordingly. Additionally, it is difficult to sufficiently grasp correct timing to apply electric charge to a droplet containing a minute particle only by grasping the break-off position. Therefore, often used is a method in which whether electric charge is correctly applied to a droplet containing a fine particle and the droplet can be sorted into a desired collection container is eventually determined by a user's visual check performed by observing the droplet applied with electric charge on a prepared specimen, and the like. Such a method requires user's expert skills, and there may be a problem in reliability and stability.

Therefore, the present disclosure is mainly directed to providing an image processing device, a fine particle sorting device, and an image processing method, in which electric charge can be easily and accurately applied to a droplet.

Solutions to Problems

To solve the above-described problem, the present disclosure provides an image processing device including:
  a control unit adapted to set a light source lighting delay time to control a light source, the light source lighting delay time indicating a time from a time point when a fine particle in fluid is detected by a detection unit until a time point when the light source is turned on for the fine particle included in a droplet formed from the fluid;
  a processing unit adapted to identify positional information of the fine particle on the basis of an image of the fine particle acquired in accordance with lighting of the light source during the set light source lighting delay time; and
  a recording unit adapted to record, in a correlated manner, the positional information identified in the processing unit and the light source lighting delay time,
  in which the processing unit determines, as a drop delay time, a light source lighting delay time correlated to target positional information that is predetermined positional information, and the drop delay time indicates a time from the time point when the fine particle is detected by the detection unit until the droplet is formed from the fluid containing the fine particle.

Next, the present disclosure provides a fine particle sorting device including:
  a detection unit adapted to detect a fine particle in fluid flowing inside a flow path;
  a light source arranged in a downstream side of the detection unit;
  a charging unit arranged in a downstream side of the light source and adapted to apply electric charge to a droplet including the fine particle included in the fluid;
  a control unit adapted to set a light source lighting delay time to control the light source, the light source lighting delay time indicating a time from a time point when a fine particle in fluid is detected by the detection unit until a time point when the light source is turned on for the fine particle included in a droplet formed from the fluid;

a processing unit adapted to identify positional information of the fine particle on the basis of an image of the fine particle acquired in accordance with lighting of the light source during the set light source lighting delay time; and a recording unit adapted to record, in a correlated manner, the positional information identified in the processing unit and the light source lighting delay time, in which the processing unit determines, as a drop delay time, a light source lighting delay time correlated to target positional information that is predetermined positional information, and the drop delay time indicates a time from the time point when the fine particle is detected by the detection unit until the droplet is formed from the fluid containing the fine particle, and the control unit controls the charging unit so as to perform charging on the basis of the drop delay time determined by the processing unit.

Next, the present disclosure provides an image processing method including:

a controlling step of setting a light source lighting delay time and controlling a light source, the light source lighting delay time indicating a time from a time point when a fine particle in fluid is detected by a detection unit until a time point when the light source is turned on for the fine particle included in a droplet formed from the fluid;

a processing step of identifying positional information of the fine particle on the basis of an image of the fine particle acquired in accordance with lighting of the light source during the set light source lighting delay time; and a recording step of recording, in a correlated manner, the positional information identified in the processing step and the light source lighting delay time, in which, in the processing step, a light source lighting delay time correlated to target positional information that is predetermined positional information is determined as a drop delay time indicating a time from the time point when the fine particle is detected by the detection unit until the droplet is formed from the fluid containing the fine particle.

Note that the "drop delay time" referred to here indicates a delay time from a clock time when a fine particle is detected by the detection unit until a droplet is formed from fluid containing the fine particle. In other words, the drop delay time indicates a necessary time from a clock time when the fine particle is detected by the detection unit until electric charge is applied to the droplet containing the fine particle by the charging unit.

In the present disclosure, the term "fine particle" broadly includes for example, biologically relevant fine particles such as a cell, a microbe, and a liposome, or synthetic particles such as a latex particle, a gel particle, and a particle for an industrial use. Additionally, the term "fine particle" includes particles that become a state of a group of fine particles when the fluid becomes a droplet. Additionally, the concept of the "fine particle" includes not only a single fine particle but also a lump of a plurality of fine particles.

Furthermore, the term "fine particle" includes a calibration bead used to adjust the drop delay time. As a product, flow cytometry particles for fine tuning cell sorters or the like is exemplified. Hereinafter, fluorescence of a calibration bead will be briefly described. When light having a predetermined wavelength is emitted to a molecule constituting a measurement sample (or a molecule adhering to a measurement sample), electrons in the molecule may be moved to an energy level corresponding to an excited state from an energy level corresponding to a ground state by utilizing energy held by the emitted light. The light emitted at this point is called excitation light. When a molecule in the ground state is excited and a singlet excited state is caused, an excited electron is moved to any energy level corresponding to the singlet excited state, but such an excited electron is moved to a lower energy level while releasing energy due to internal conversion. When the electrons in the excited state returns to the ground state, energy may be emitted as light, and the light emitted at this point is fluorescence. A calibration bead used for drop delay time adjustment has a characteristic of using a fluorescent substance having high fluorescence sensitivity such that fluorescence can be detected even by an imaging element like a CCD.

Additionally, the term "biologically relevant fine particle" includes a chromosome, a liposome, a mitochondria, an organelle (cell organ), and the like constituting various kinds of cells. The term "cell" includes an animal cell (such as hematopoietic cell) and a plant cell. The term "microbe" includes for example, bacteria such as colibacillus, viruses such as a tobacco mosaic virus, and fungi such as yeast. Additionally, the term "biologically relevant fine particle" includes biologically relevant polymers such as a nucleic acid, a protein, and a complex thereof. Furthermore, the particle for an industrial use may be, for example, an organic or inorganic polymer material, a metal, or the like. The organic polymer material includes polystyrene, styrene-divinylbenzene, polymethyl methacrylate, and the like. The inorganic polymer material includes glass, silica, a magnetic material, and the like. The metal includes gold colloid, aluminum, and the like. These fine particles generally have a spherical shape, but may also have a non-spherical shape, and furthermore, a size, mass, and the like thereof are not particularly limited.

Effects of the Invention

According to the present disclosure, provided are the image processing device, fine particle sorting device, and image processing method, in which electric charge can be easily and accurately applied to a droplet.

Note that effects recited herein are not necessarily limited and may be any one of those recited in the present disclosure.

BRIEF DESCRIPTION OF DRAWINGS

FIG. 3 provides schematic views to describe a configuration of an orifice 21 of the microchip 2. (A) illustrates a schematic top view, (B) illustrates a schematic cross-sectional view, and (C) illustrates a front view.

FIG. 5 provides views illustrating exemplary images acquired by a light source 41. (A) illustrates an exemplary droplet image acquired by an LED light source, and (B) illustrates an exemplary fine particle image acquired by a laser light source.

FIG. 6 provides explanatory diagrams illustrating a specific example in which a processing unit 73 calculates positional information of a fine particle by probability statistical processing on the basis of luminance information of an image of the fine particle. (A) illustrates observation data of the luminance information, and (B) illustrates a luminance center position value by the probability statistical processing.

MODE FOR CARRYING OUT THE INVENTION

Preferred embodiments to implement the present disclosure will be described below with reference to the drawings. Note that the embodiments described below illustrate examples of representative embodiments of the present disclosure and the scope of the present disclosure should not be interpreted in a manner limited by the embodiments. The description will be provided in the following order.

1. Fine Particle Sorting Device and Image Processing Method According to First Embodiment of Present Disclosure
  (1-1) Charging Unit
  (1-2) Microchip
  (1-3) Detection Unit
  (1-4) Droplet Camera
  (1-5) Deflection plate
  (1-6) Collection Container
  (1-7) Image Processing Device
  (1-7-1) Control Unit
  (1-7-2) Recording Unit
  (1-7-3) Processing Unit
  (1-8) Image Processing Method
  (1-8-1) Reference Drop Delay Time Setting Step S1
  (1-8-2) Positional Information Identifying Step S2
  (1-8-3) Imaging Controlling Step S3
  (1-8-4) Correlation Equation Calculating Step S4
  (1-8-5) Drop Delay Time Determining Step S5

2. Image Processing Method According to Second Embodiment of Present Disclosure
  (2-1) Temporary Drop Delay Time Determining Step T1
  (2-2) Step of Acquiring Number of Bright Spots T2
  (2-3) Step of Ranking Number of Bright Spot T3
  (2-4) Reference Drop Delay Time Setting Step T4
  (2-5) Positional Information Identifying Step T5
  (2-6) Imaging Controlling Step T6
  (2-7) Correlation Equation Calculating Step T7
  (2-8) Drop Delay Time Determining Step T8

Figure 1:
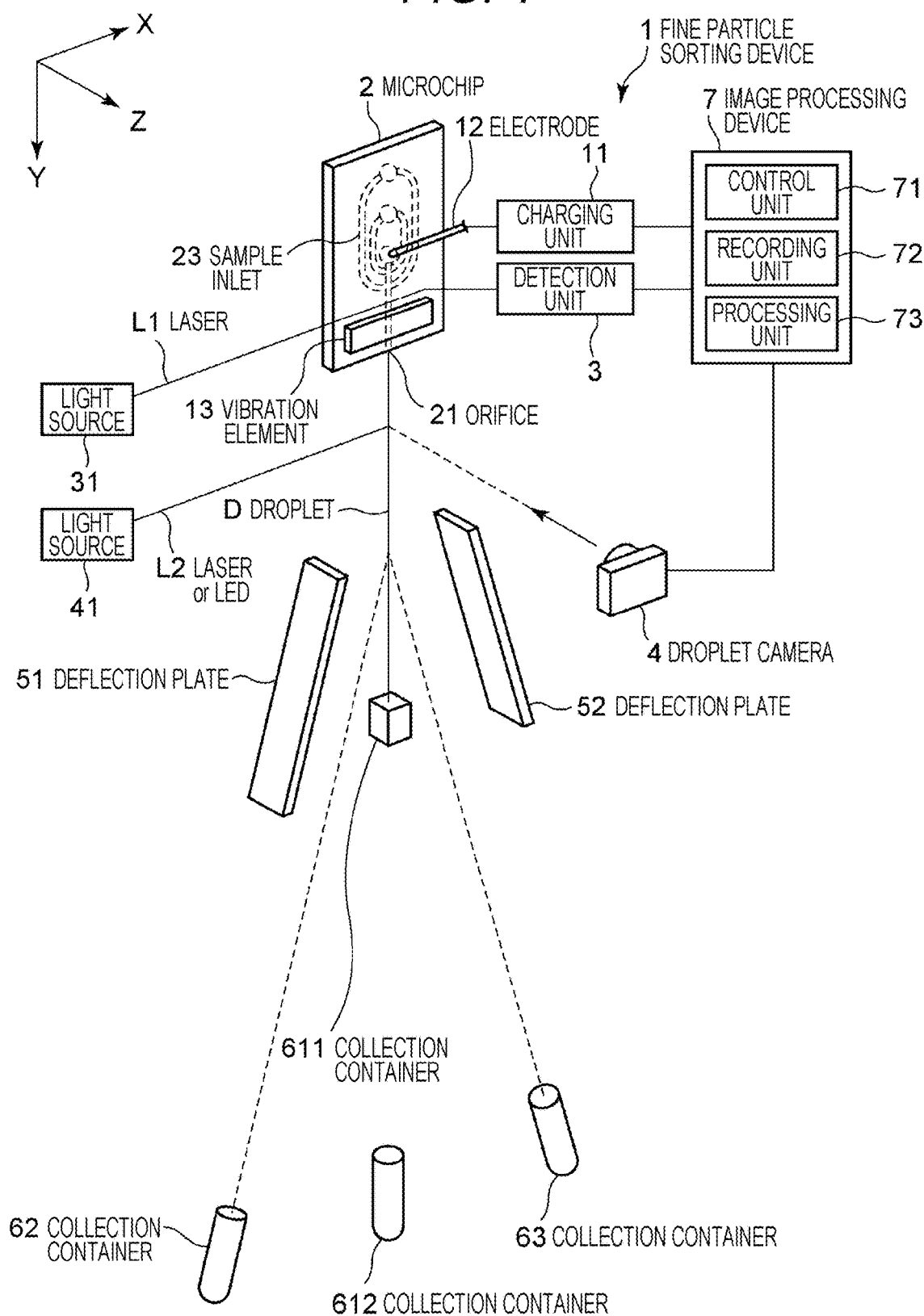
FIG. 1 is a schematic view to describe a configuration of a sorting system of a fine particle sorting device 1 formed as a microchip type flow cytometer (flow cytometer 1) according to a first embodiment of the present disclosure.

1. Device Configuration of Fine Particle Sorting Device according to First Embodiment of Present Disclosure FIG. 1 is a schematic view illustrating a configuration of a sorting system in a fine particle sorting device 1 formed as a microchip type flow cytometer (hereinafter also referred to as "flow cytometer 1") according to the present disclosure.

(1-1) Charging Unit

The flow cytometer 1 includes a charging unit 11 that applies electric charge to a droplet discharged from an orifice 21 formed at a microchip 2. The charging unit 11 is arranged in an upstream side of a droplet camera 4 and applies electric charge to a droplet including a fine particle included in fluid. Electric charge to the droplet is performed by an electrode 12 electrically connected to the charging unit 11 and inserted into a sample inlet 23 provided in the microchip 2. Note that the electrode 12 is at least inserted into any place of the microchip 2 so as to electrically contact sample liquid or sheath liquid fed through a flow path.

In the flow cytometer 1, the charging unit 11 can electrically charge a droplet containing a fine particle after a drop delay time has elapsed from when the fine particle included in the sample liquid is detected by a detection unit 3 described later. The drop delay time referred to here indicates a delay time from a clock time when a fine particle is detected by the detection unit 3 until a droplet is formed from fluid containing the fine particle. In other words, the drop delay time indicates a necessary time from the clock time when the fine particle is detected by the detection unit 3 until electric charge is applied to the droplet containing the fine particle by the charging unit 11.

(1-2) Microchip

Figure 2:
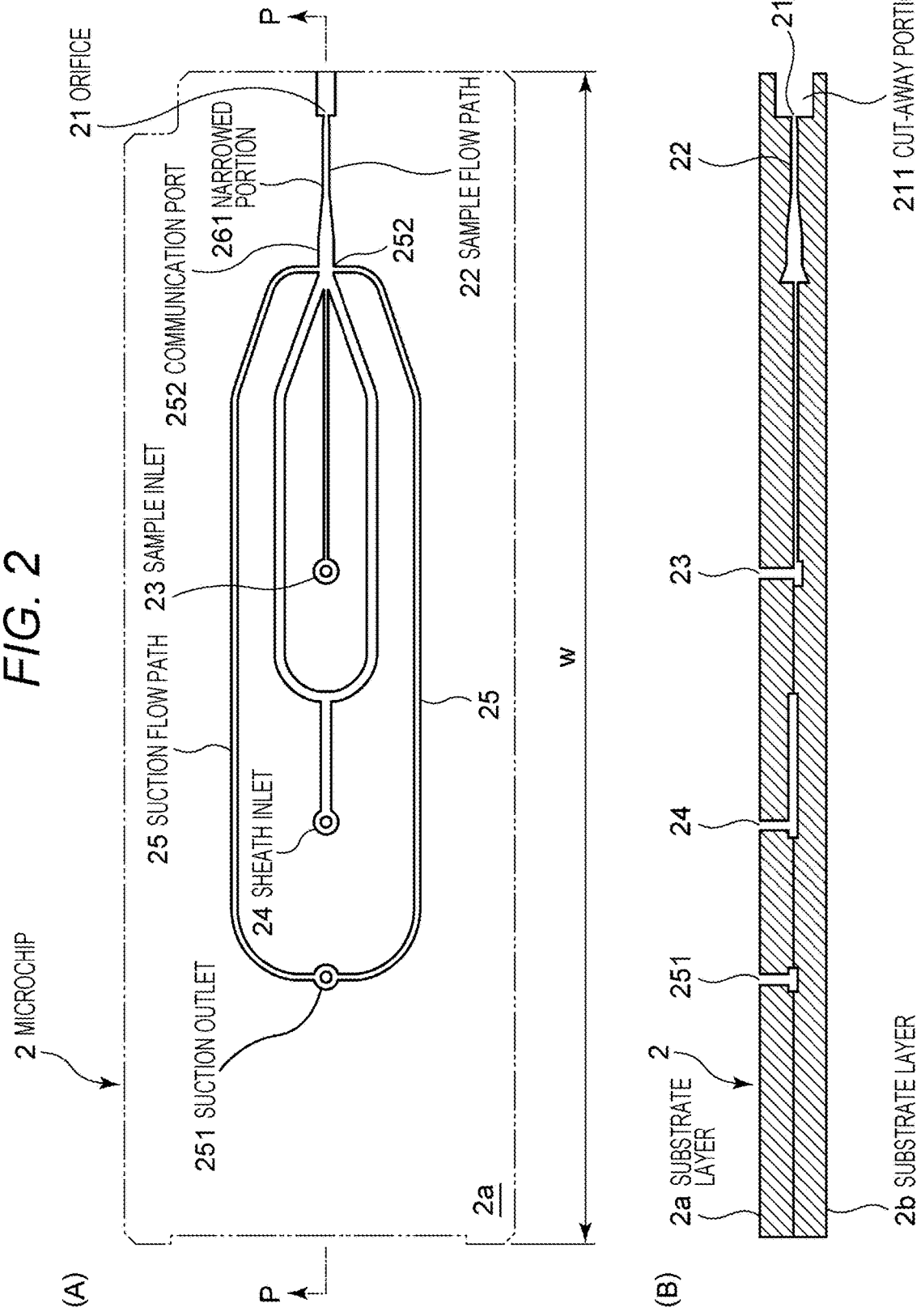
FIG. 2 provides schematic views to describe an exemplary configuration of a microchip 2 that can be mounted on the flow cytometer 1. (A) illustrates a schematic top view, and (B) illustrates a schematic cross-sectional view corresponding to a cross-section P-P in (A).

FIGS. 2 and 3 illustrate an exemplary microchip 2 that can be mounted on the flow cytometer 1. FIG. 2(A) is a schematic top view, and (B) is a schematic cross-sectional view corresponding to a cross-section P-P in (A). Additionally, FIG. 3 provides views to schematically describe a configuration of the orifice 21 of the microchip 2, (A) illustrates a schematic top view, (B) illustrates a schematic cross-sectional view, and (C) illustrates a front view. FIG. 3(B) corresponds to the cross-section P-P in FIG. 2(A).

The microchip 2 is obtained by bonding substrate layers 2a and 2b on which a sample flow path 22 is formed. The sample flow path 22 can be formed on the substrate layers 2a and 2b by performing injection molding with a thermoplastic resin by using a mold. As the thermoplastic resin, it may be possible to adopt plastic known as a material of a microchip in the related art, such as polycarbonate, polymethylmethacrylate resin (PMMA), cyclic polyolefin, polyethylene, polystyrene, polypropylene, and polymethyldisilazane (PDMS).

The sample liquid is introduced into the sample inlet 23 from a liquid feeding connector portion, and joined with the sheath liquid introduced from the liquid feeding connector portion into a sheath inlet 24, and then fed through the sample flow path 22. The sheath liquid introduced from the sheath inlet 24 is separated and fed in two directions, and then joined with the sample liquid in a manner interposing the sample liquid between the two directions at a joint portion where the sample liquid introduced from the sample inlet 23 is joined. Consequently, a three-dimensional laminar flow in which the sample liquid laminar flow is positioned in the middle of sheath liquid laminar flows is formed at the joint portion.

Reference sign 25 indicates a suction flow path that temporarily reverses a flow by applying negative pressure to the inside of the sample flow path 22 and eliminate clogging or air bubbling when such clogging or air bubbling occurs in the sample flow path 22. The suction flow path 25 has one end formed with a suction outlet 251 connected to a negative pressure source such as a vacuum pump via the liquid feeding connector portion, and has the other end connected to the sample flow path 22 at a communication port 252.

A laminar flow width of the three-dimensional laminar flow is narrowed at narrowed portions 261 (refer to FIG. 2) and 262 (refer to FIG. 3) formed so as to gradually reduce a vertical cross-section area in a direction from an upstream side to a downstream side of a liquid feeding direction. After that, the three-dimensional laminar flow is ejected as a fluid stream (refer to FIG. 1) from the orifice 21 provided at one end of the flow path. In FIG. 1, an ejecting direction of the fluid stream from the orifice 21 is indicated by a Y-axis positive direction.

A connecting portion of the sample flow path 22 to the orifice 21 is a straight portion 27 linearly formed. The straight portion 27 functions in order to inject the fluid stream straightly in the Y-axis positive direction from the orifice 21.

The fluid stream injected from the orifice 21 is made into a droplet by vibration applied to the orifice 21 by a chip vibrating unit in accordance with a droplet frequency (Droplet CLK). The orifice 21 is opened in a direction to end faces of the substrate layers 2a and 2b, and a cut-away portion 211 is provided between the opened position and the end faces of the substrate layers. The cut-away portion 211 is formed by cutting the substrate layers 2a and 2b between the opened position of the orifice 21 and the substrate end faces such that a diameter L of the cut-away portion 221 becomes larger than an opened diameter 1 of the orifice 21 (refer to FIG. 3(C)). Preferably, the diameter L of the cut-away portion 211 is formed twice or more than the open diameter 1 of the orifice 21 so as not to hinder movement of a droplet discharged from the orifice 21.

(1-3) Detection Unit

Reference sign 3 in FIG. 1 indicates a detection unit to detect current light subjected to measurement and being generated from a fine particle of a cell or the like by irradiation with a laser L1 emitted from the light source 31. The detection unit 3 detects a fine particle in fluid flowing through the flow path. The detection unit 3 detects a characteristic of a cell between the narrowed portion 261 (refer to FIG. 2) and the narrowed portion 262 (refer to FIG. 3) of the sample flow path 22. Such characteristic detection is not particularly limited, but in a case of optical detection, for example, scattered light or fluorescence generated from a cell is detected by the detection unit 3 when the laser L1 (refer to FIG. 1) irradiates cells that are made to flow inside the sample flow path 22 in a manner aligned in a center of the three-dimensional laminar flow.

For such light irradiation and detection, a condenser lens to collect laser beams and irradiate a cell and a light emitting system such as a dichroic mirror or a band pass filter may also be included in addition to the laser light source. A detection system includes, for example, a photo multiplier tube (PMT), an area imaging element such as a CCD or a CMOS device, and the like.

Light subjected to measurement and detected by the detection system of the detection unit 3 is light generated from a cell by irradiation with measurement light, and it may be possible to use, for example, scattered light such as forward scattered light, lateral scattered light, scattered light of Rayleigh scattering, or scattered light of Mie scattering. Such light subjected to measurement is converted into an electric signal, output to a control unit 71, and used to determine an optical characteristic of a cell.

Note that the detection unit 3 may also magnetically or electrically detect a characteristic of a cell. In this case, a microelectrode is disposed in a manner facing the sample flow path 22 of the microchip 2, and a resistance value, a capacity value (capacitance value), an inductance value, impedance, a changed value of an electric field between electrodes, or magnetization, magnetic field change, magnetic flux change, and the like are measured.

(1-4) Droplet Camera

Reference sign 4 in FIG. 1 is an exemplary imaging unit of the present disclosure and also is a droplet camera such as a CCD camera or a CMOS sensor in order to image a droplet D discharged from the orifice 21 of the microchip 2. The droplet camera 4 is arranged in a downstream side of the detection unit 3, and images at least a part of fluid. The droplet camera 4 is designed so as to be able to adjust a focal point of an image of the imaged droplet D. A light source 41 described later is used as a light source for the droplet camera 4 to perform imaging.

Furthermore, in the flow cytometer 1, when a microchip is replaced with a new one or when external environment (air temperature or the like) is changed, it may be necessary to change parameters (sheath pressure, droplet frequency, piezo driving pressure, and the like) to form a droplet. In this case, it is necessary to adjust a time from when a fine particle is detected by the detection unit 3 until a droplet containing the fine particle is electrically charged (hereinafter such a time may be referred to as a drop delay time).

Additionally, an image captured by the droplet camera 4 is displayed on a display unit such as a display, and can be utilized by a user to confirm a forming state of a droplet D (size, shape, interval, and the like of the droplet) at the orifice 21.

The light source 41 is controlled by the control unit 71 described later. The light source 41 includes an LED to image a droplet and a laser L2 (e.g., red laser light source) to image a fine particle, and a light source to be used is switched by the control unit 71 in accordance with an imaging object. A specific structure of the light source 41 is not particularly limited, and one kind or two or more kinds of known circuits or elements can be selected and freely combined as far as the effect of the present disclosure is not impaired.

Figure 4:
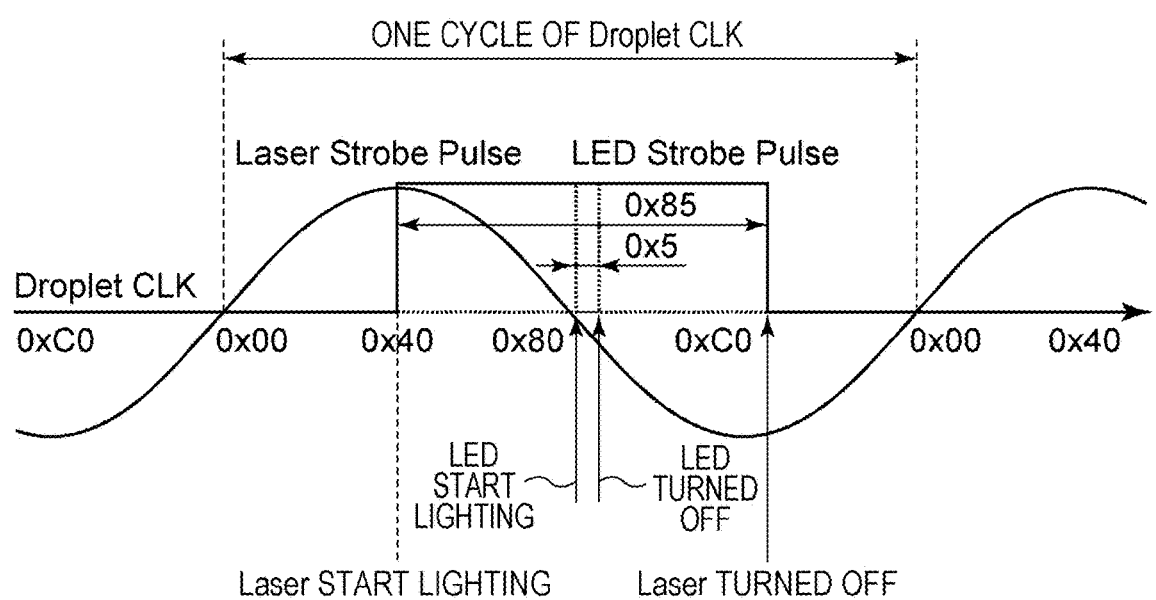
FIG. 4 is an exemplary waveform diagram illustrating a relation between a droplet frequency (Droplet CLK) and light source lighting/lighting-out timing.

FIG. 4 is an exemplary waveform diagram illustrating a relation between a droplet frequency (Droplet CLK) and light source lighting/lighting-out timing.

In a case of using the LED as the light source 41, a droplet can be imaged by the droplet camera 4. As illustrated in FIG. 4, the LED emits light only for a very short time out of one cycle of the Droplet CLK. This light emission is performed per the Droplet CLK, and a specific moment of forming a droplet can be extracted and acquired as an image by this light emission. The Droplet CLK is about 10 to 50 kHz while imaging by the droplet camera 4 is performed about 60 times per second, and an acquired droplet image is an image in which about one thousand of droplets are accumulated.

In a case of using the laser L2 as the light source 41, a fine particle can be imaged by the droplet camera 4. As illustrated in FIG. 4, the laser L2 emits light for about half a cycle of the Droplet CLK. At this point, only in a case where a fine particle is detected by the detection unit 3, fluorescence of the fine particle included in a droplet can be acquired from an image by making the laser L2 emit light after elapse of a light source lighting delay time set by the control unit 71. Since imaging by the droplet camera 4 is performed about 60 times per second and measurement is executed such that detection of a fine particle and light emission of the laser L2 light source are performed several thousand times per second, a stable fine particle image in which fluorescence of about tens of fine particles is accumulated can be acquired. Meanwhile, a light emission time of the laser L2 may be any time as far as a stable fine particle image can be acquired.

FIG. 5 provides exemplary images acquired by the light source 41. FIG. 5(A) illustrates an exemplary droplet image acquired by the LED light source. FIG. 5(B) illustrates an exemplary fine particle image acquired by the laser light source.

(1-5) Deflection plate

Reference signs 51 and 52 in FIG. 1 indicate a pair of deflection plates facing each other and arranged in a manner interposing a droplet D injected from the orifice 21 and imaged by the droplet camera 4. Each of the deflection plates 51 and 52 has a configuration including an electrode that controls a moving direction of the droplet discharged from the orifice 21 by electric action force with the electric charge applied to the droplet. Additionally, the deflection plates 51 and 52 also control a trajectory of the droplet D generated from the orifice 21 by the electric action force with the electric charge applied to the droplet D. In FIG. 1, the facing direction of the polarization plates 51 and 52 is indicated by the X-axis direction.

(1-6) Collection Container

In the flow cytometer 1, a droplet D is received by any one of a plurality of collection containers 611, 612, 62, and 63 disposed in a line in the facing direction (X-axis direction) of the deflection plates 51 and 52. The collection containers 611, 612, 62, and 63 may be general purpose plastic tubes or glass tubes used in experiments. The number of the collection containers 611, 612, 62, and 63 is not particularly limited, but four collection containers are illustrated here. The droplet D generated from the orifice 21 is guided to and collected in any one of the four collection containers 611, 612, 62, and 63 in accordance with presence or magnitude of the electric action force between the deflection plates 51 and 52.

The collection containers 611, 612, 62, and 63 are installed in a container for a collection container (not illustrated) in an exchangeable manner. The container for a collection container (not illustrated) is disposed on a Z-axis stage (not illustrated) having a configuration movable in a direction (Z-axis direction) orthogonal to: the ejecting direction (Y-axis direction) of the droplet D from the orifice 21; and the facing direction (X-axis direction) of the polarization plates 51 and 52.

(1-7) Image Processing Device

As illustrated in FIG. 1, the flow cytometer 1 includes an image processing device 7 in addition to the above-described components. The image processing device 7 can include a general-purpose computer including a CPU, a memory, a hard disk, and the like, and an OS and a program and the like to execute respective steps related to an image processing method described next are stored in the hard disk.

The image processing device 7 according to the present disclosure roughly includes the control unit 71, a recording unit 72, and a processing unit 73. Each of the units will be described in detail below.

(1-7-1) Control Unit

The control unit 71 sets a light source lighting delay time indicating a time from a time point when a fine particle in fluid is detected by the detection unit 3 until a time point when a light source is turned on for the fine particle included in a droplet formed from the fluid, and controls the light source 41 and the droplet camera 4 such that the fine particle is imaged by the droplet camera 4 arranged in the downstream side of the detection unit 3.

The control unit 71 controls the charging unit 11 so as to apply electric charge on the basis of a drop delay time determined by the processing unit 73 described later.

(1-7-2) Recording Unit

The recording unit 72 records, in a correlated manner, positional information identified in the processing unit 73 and the light source lighting delay time. The recording unit 72 can include various kinds of IC memories such as a RAM and a ROM.

(1-7-3) Processing Unit

The processing unit 73 identifies positional information of a fine particle on the basis of an image of the fine particle acquired in accordance with lighting of the light source 41 during the light source lighting delay time set by the control unit 71. The positional information can be calculated on the basis of a gravity center on a binary image generated from the acquired image of the plurality of fine particles. Also, the positional information can be calculated by probability statistical processing on the basis of luminance information of the acquired image of the plurality of fine particles. The acquired image here can be an image in which layers of fluorescence from the plurality of fine particles are stacked as described above. Also, it may be possible to use an image in which a plurality of images acquired during the same light source lighting delay time is accumulated.

FIG. 6 provides explanatory diagrams illustrating a specific example in which the processing unit 73 calculates positional information of a fine particle by the probability statistical processing on the basis of luminance information of an image of a fine particle. In a case where observation data (luminance information) like FIG. 6(A) is obtained, when a kind of probability model that the observation data follows is known, distribution parameter (average and dispersion) thereof can be estimated from by maximum likelihood estimation. In the observation data, a luminance value is proportional to the number of fine particles (such as calibration beads) at a pixel position thereof. It is assumed that positional dispersion of the calibration beads within the observation data is dependent on flow rate dispersion of the calibration beads and the flow rate dispersion follows normal distribution. Therefore, a luminance center position value can be accurately estimated by the maximum likelihood estimation as illustrated in FIG. 6 (B). The luminance center position here indicates a center position of the luminance on the observation data. This luminance center position is to be the positional information of the fine particle to be calculated.

Furthermore, the processing unit 73 determines, as a drop delay time, a light source lighting delay time correlated to target positional information that is predetermined positional information, and the drop delay time indicates a time from the time point when the fine particle is detected by the detection unit 3 until a droplet is formed from fluid containing the fine particle.

Figure 7:
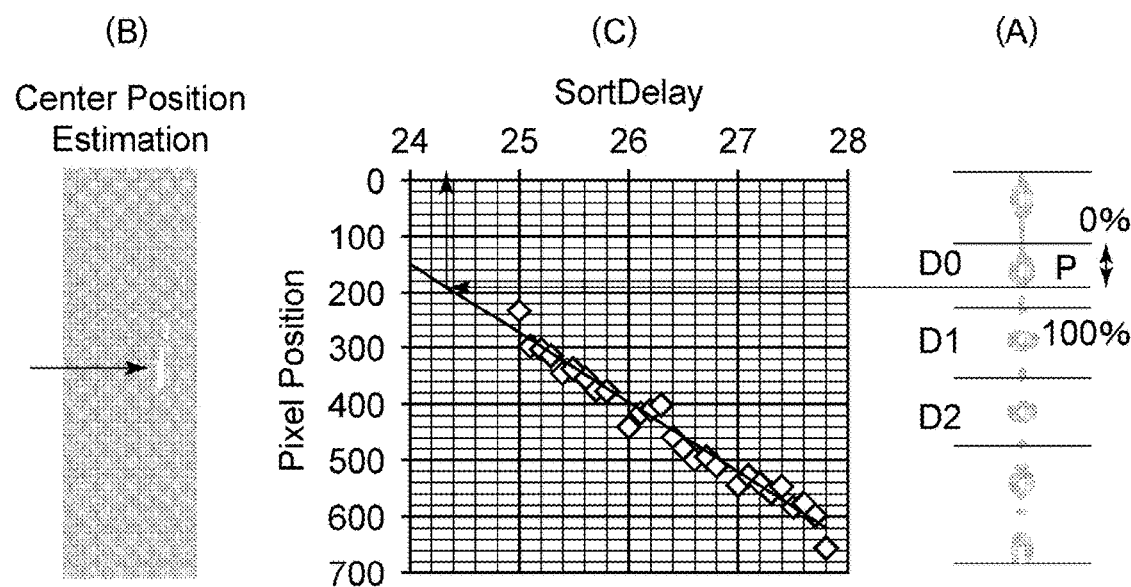
FIG. 7 provides diagrams illustrating an exemplary setting method for target positional information. (A) is a photographic view illustrating an exemplary image of a plurality of fine particles including a fine particle acquired during a predetermined time in which a light source lighting delay time is set. (B) is a photographic view illustrating an exemplary binary image generated from the image of the plurality of fine particles. (C) is an exemplary plot diagram in which positional information of a fine particle and a light source lighting delay time during which the positional information is acquired are set as variables.
Figure 8:
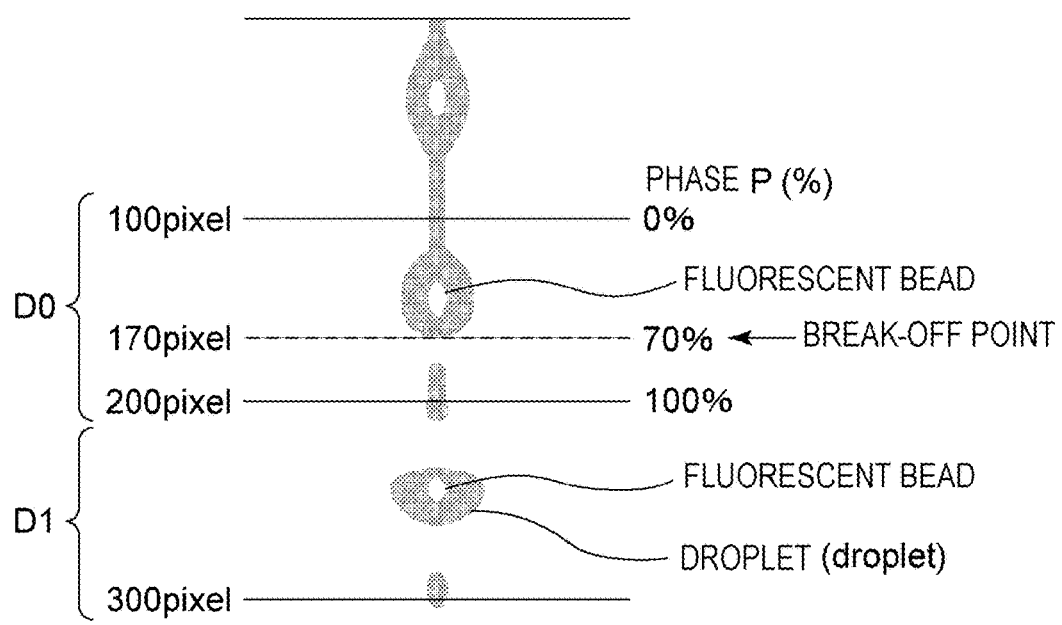
FIG. 8 is a diagram illustrating an exemplary setting method for target positional information and also is an enlarged view of FIG. 7(A).

FIGS. 7 and 8 are explanatory diagrams illustrating an exemplary method of determining, as a drop delay time, a light source lighting delay time correlated to target positional information. Furthermore, FIG. 8 is an enlarged view of FIG. 7(A). FIG. 7(A) is a photographic view illustrating an exemplary image of a plurality of fine particles including the fine particle acquired during a predetermined time in which the light source lighting delay time is set, and illustrates a state in which the image is divided into droplet regions D0 to D2.

Figure 9:
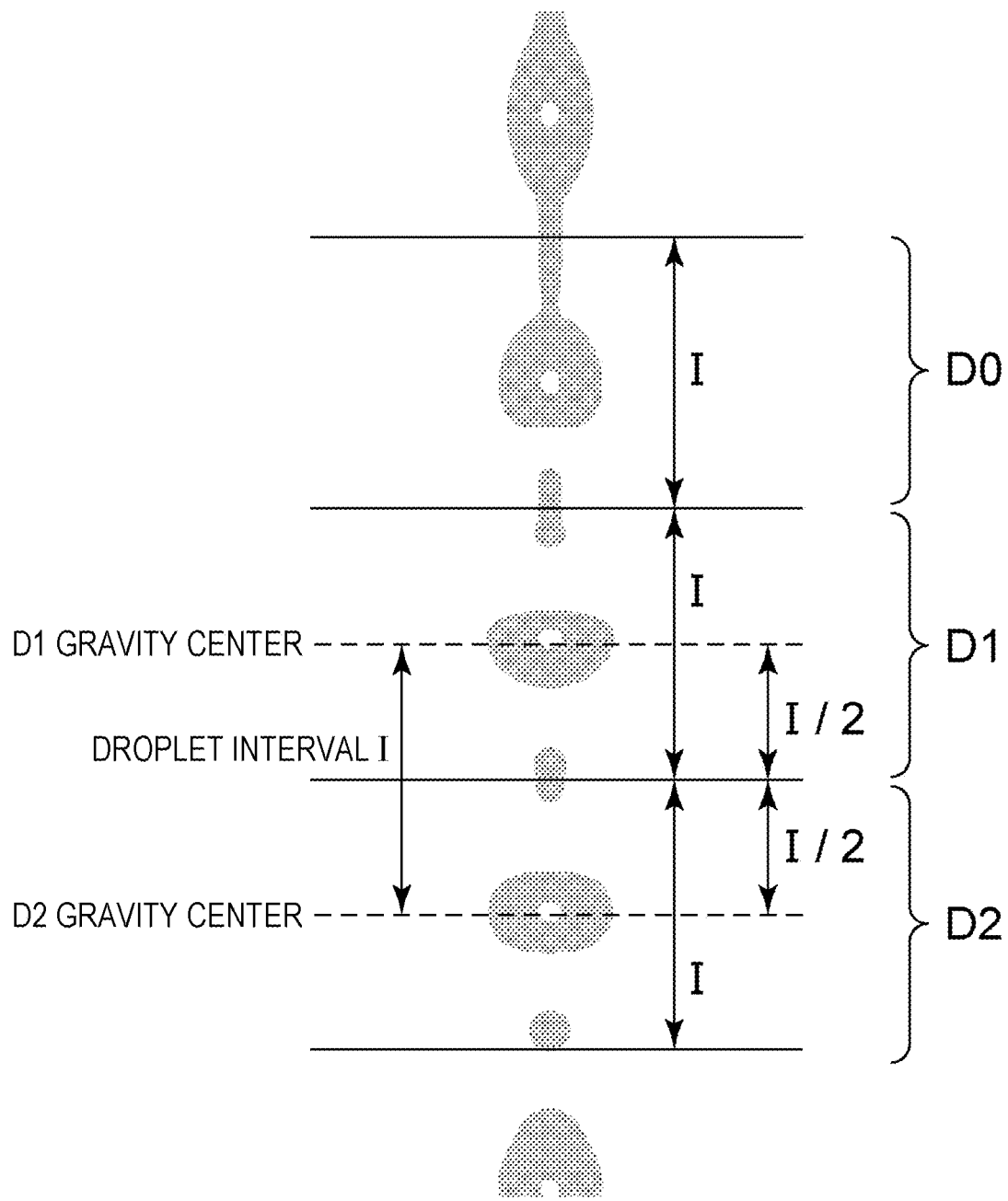
FIG. 9 is a diagram to describe division into droplet regions D0 to D2 by using gravity center positions of droplets D1 and D2 in a droplet image.

FIG. 9 is a diagram to describe division into droplet regions D0 to D2 by using gravity center positions of droplets D1 and D2 in a droplet image. The division into the droplet regions D0 to D2 is performed by using the gravity center positions of the droplets D1 and D2 in the droplet image as illustrated in FIG. 9, for example. A droplet interval I is calculated from gravity center positions of the droplets D1 and D2, and a region having the interval I centering the gravity center of the droplet D1 is to be the droplet region D1 and a region having the interval I centering the gravity center of the droplet D2 is to be the droplet region D2. A region having the interval I and adjacent to an upper portion of D1 is to be a droplet region D0.

FIG. 7(B) is a photographic view illustrating an exemplary binary image generated from the image of the plurality of fine particles. The processing unit 73 generates the binary image on the basis of the acquired image of the fine particles, and the control unit 71 performs control so as to display the binary image on the display unit. For example, the binary image is captured when fluorescence enters the droplet camera 4 from a group of fine particles contained in the droplet D irradiated and excited by the laser L2. The binary image is acquired as a lump of pixels each having a gradation value higher than a predetermined threshold in the image of the droplet D imaged by the droplet camera 4, and the gravity center position thereof is to be positional information of the fine particle. Meanwhile, as described above, the positional information of the fine particle can also be calculated from luminance information of an image by the probability statistical processing, and more accurate calculation for the positional information is expected.

FIG. 7(C) is an exemplary plot diagram generated by the processing unit 73. The processing unit 73 generates a plot diagram in which positional information and a light source lighting delay time are set as variables on the basis of a plurality of different light source lighting delay times recorded in the recording unit 72 and positional information recorded in a manner correlated to each of the plurality of different light source lighting delay times. The control unit 71 may perform control so as to display the plot diagram on the display unit. The processing unit 73 calculates a correlation equation between positional information and a light source lighting delay time on the basis of the plurality of different light source lighting delay times recorded in the recording unit 72 and the positional information recorded in a manner correlated to each of the plurality of different light source lighting delay times. Since the correlation equation is a linear equation, calculation can be performed with high accuracy by a least-squares method, for example. The processing unit 73 determines, as a drop delay time, a light source lighting delay time identified on the basis of the target positional information and the correlation equation.

As illustrated in FIG. 8, the positional information (pixel position): 100 (pixel) to 200 (pixel) of fine particles (calibration beads) in the image region D0 is converted to a phase P(%): 0(%) to 100(%). In this example, a phase 70% illustrated in FIG. 8 corresponds to the target positional information, namely, a pixel position: 170 (pixel) illustrated in FIG. 7(C). Meanwhile, the target positional information 170 (pixel) is a position where a droplet D starts to be formed in the Y-axis positive direction illustrated in FIG. 1 (hereinafter referred to as a break-off point). The target positional information is preliminarily stored in the recording unit 72 as positional information that enables highly accurate sorting of a fine particle.

As illustrated in FIG. 7(C), the processing unit 73 determines, as a drop delay time, a light source lighting delay time (sort delay (about 24.4)) correlated to the target positional information (pixel position: 170 (pixel)). In other words, the processing unit 73 converts the target positional information (pixel position: 170 (pixel)) into the light source lighting delay time (sort delay (about 24.4)) by using the plot diagram illustrated in FIG. 7(C). Then, the processing unit 73 determines the light source lighting delay time as the drop delay time.

Meanwhile, the droplet image illustrated in FIG. 7(A), the binary image illustrated in FIG. 7(B), and the plot diagram illustrated in FIG. 7(C) may also be simultaneously displayed on the display unit. Such display is suitable for a case where a user visually recognizes a state in which calculation of the correlation equation and determination of the drop delay time are performed.

(1-8) Image Processing Method

Figure 10:
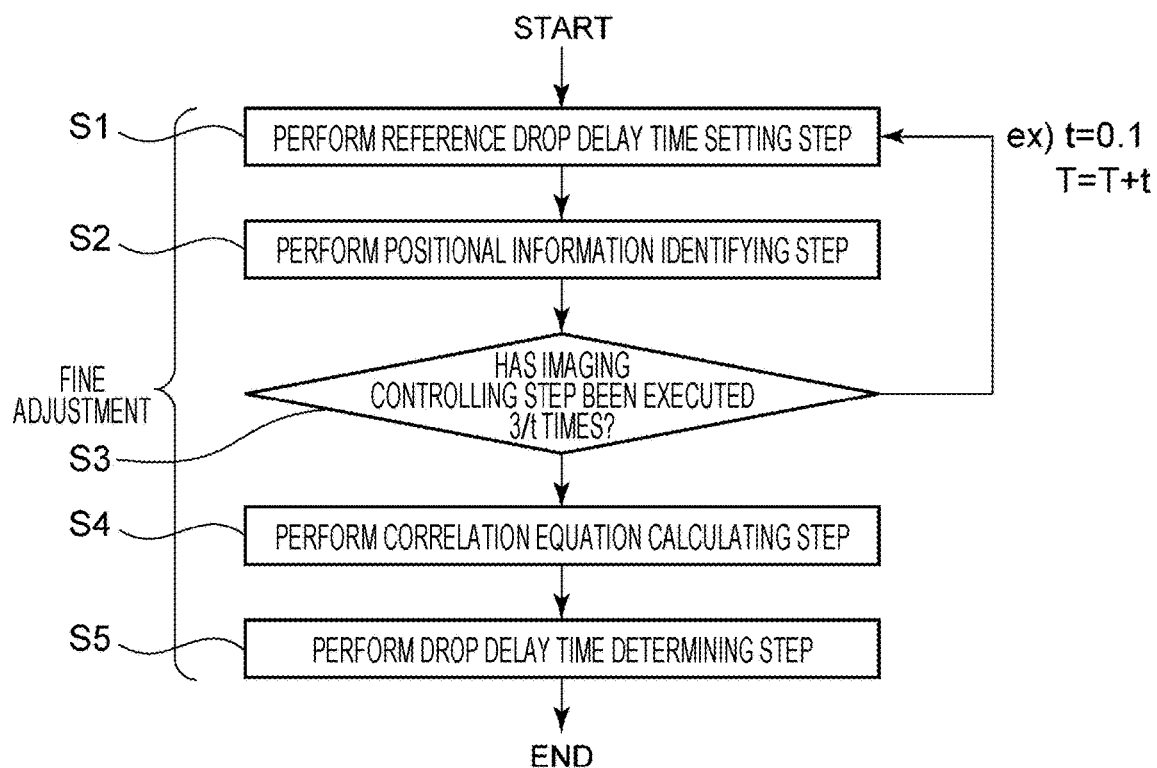
FIG. 10 is a flowchart to describe an image processing method according to the first embodiment of the present disclosure.

FIG. 10 is a flowchart to describe an image processing method. The image processing method includes steps S1 to S5. Respective steps S1 to S5 are steps to perform fine adjustment for a light source lighting delay time and determine a drop delay time. Specifically, in respective steps S1 to S5, fine adjustment is performed for a reference drop delay time acquired as a rough value by coarse adjustment for the light source lighting delay time. Each of the procedures will be described in the following. Note that the respective steps S1 to S5 are calibration processes in order to determine the drop delay time starting from when a current cell or the like is detected by the detection unit 3 until the charging unit 11 applies electric charge to a droplet D containing the cell or the like. Therefore, as the fine particle, it is preferable to use a calibration bead such as a particle for an industrial use in which a shape and the like of the particle is known in advance.

(1-8-1) Reference Drop Delay Time Setting Step S1

First, in step S1, the control unit 71 sets a reference drop delay time. Here, the reference drop delay time indicates a time temporarily deemed as a drop delay time until the drop delay time is determined in step S5 described later, and also indicates a light source lighting delay time. As the reference drop delay time, for example, values of 24 to 28 are set.

(1-8-2) Positional Information Identifying Step S2

In step S2, the processing unit 73 identifies, as the positional information, a center position of luminance calculated by the maximum likelihood estimation from a fine particle image captured by the droplet camera 4.

(1-8-3) Imaging Controlling Step S3

In step S3, imaging by the droplet camera 4 is repeatedly performed the number of times (e.g., 30 times) equivalent to a value obtained by a following calculation: number N of droplets D continuous in the positive Y-axis direction illustrated in FIG. 1 (e.g., 3 pieces)/a droplet clock change interval t (e.g., 0.1). Note that the number of imaging times performed by the droplet camera 4 and the droplet clock change interval t are not limited to the above-mentioned values, and may be any values sufficient to acquire correlation between the positional information and the light source lighting delay time.

Meanwhile, in steps S2 and S3 described above, the case where the processing unit 73 calculates a luminance center position value by using the maximum likelihood estimation has been described, but the present disclosure is not limited to this example. For example, the processing unit 73 can generate a binary image on the basis of an acquired image and calculate a gravity center on the binary image as a luminance center position.

(1-8-4) Correlation Equation Calculating Step S4

In step S4, the processing unit 73 calculates a correlation equation between the positional information and the light source lighting delay time on the basis of the plurality of different light source lighting delay times recorded in the recording unit 72 and the positional information recorded in a manner correlated to each of the plurality of different light source lighting delay times. The method of calculating the correlation equation is not particularly limited, and for example, a known least-squares method can be used. For example, the correlation here includes correlation between information of a position where a droplet D starts to be formed in the positive Y-axis direction illustrated in FIG. 1 (hereinafter referred to as a break-off point) and a light source lighting delay time during which the positional information is acquired.

(1-8-5) Drop Delay Time Determining Step S5

In step S5, the processing unit 73 determines, as a drop delay time, a light source lighting delay time identified on the basis of the target positional information and the correlation equation.

In a cell sorter, it may be very important to accurately calculate a delay time (drop delay time) from a clock time when the detection unit 3 detects a fine particle until a droplet is formed from fluid containing the fine particle in terms of improving a collection rate and purity. In the present disclosure, the drop delay time can be easily and calculated with high accuracy by utilizing the correlation between positional information of a fine particle and a light source lighting delay time during which the positional information is acquired.

2. Image Processing Method According to Second Embodiment of Present Disclosure

Figure 11:
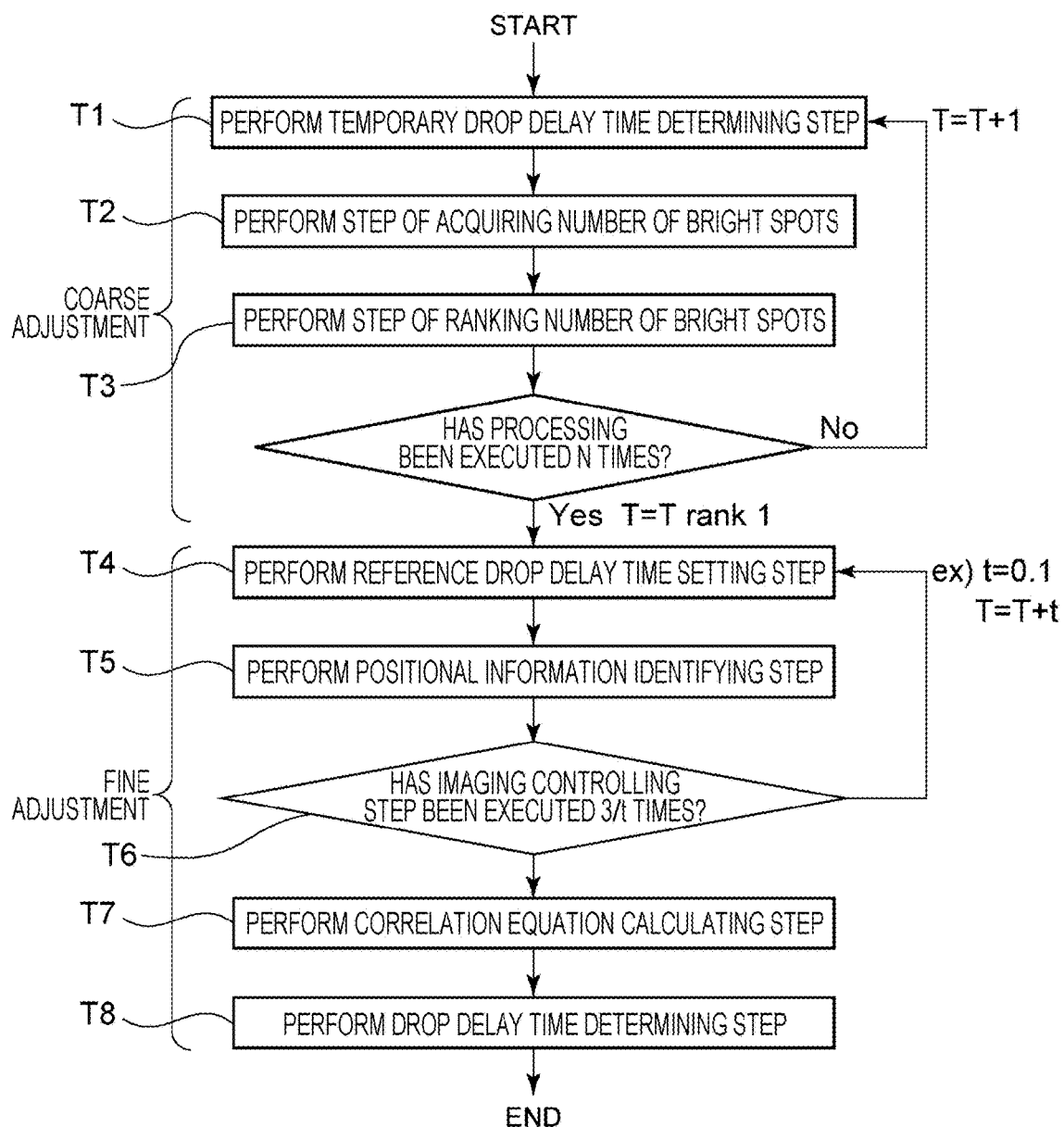
FIG. 11 is a flowchart to describe an image processing method according to a second embodiment of the present disclosure.

Next, an image processing method according to a second embodiment of the present disclosure will be described. FIG. 11 is a flowchart to describe an image processing method according to the second embodiment of the present disclosure. The image processing method includes procedures of steps T1 to T8. The image processing method of the present disclosure includes two steps: a coarse adjustment step (steps T1 to T3); and a fine adjustment step (T4 to T8). The respective procedures will be described in the following. Note that steps T4 to T8 illustrated in FIG. 11 are the same as steps S1 to S5 in FIG. 10. In this flow, when repetitive processing corresponding to steps T1 to T3 is completed, steps T4 to T8 are subsequently executed.

In this flow, the repetitive processing corresponding to steps T1 to T3 is repeated up to the number of times N (e.g., 20 to 40) equal to the number of pieces of data to be ranked.

(2-1) Temporary Drop Delay Time Determining Step T1

In step T1, a processing unit 73 determines a temporary drop delay time. Here, the temporary drop delay time indicates a time temporarily deemed as a drop delay time until the drop delay time is determined by the drop delay time determining step T8.

(2-2) Step of Acquiring Number of Bright Spots T2

In step T2, the processing unit 73 divides a droplet image into three droplet regions D0 to D2 (refer to FIG. 7(A)) and then acquires the number of bright spots in the region D0 by sequentially a changing the temporary drop delay time T in increments of 1. Meanwhile, the bright spot indicates a pixel having luminance higher than a predetermined threshold in an image of a droplet D imaged by a droplet camera 4, and also is image information of a fine particle contained in the droplet D irradiated and excited by a laser L2.

(2-3) Step of Ranking Number of Bright Spots T3

In step T3, the processing unit 73 ranks the number of bright spots in the region D0 by comparing a plurality of images of droplets D imaged by the droplet camera 4 at an interval of a droplet clock, and then determines, as a reference drop delay time, a temporary light source lighting delay time from a time point t0 when one fine particle is detected by a detection unit 3 out of a plurality of fine particles in the fluid until a time point when the number of bright spots within the region D0 becomes maximal.

(2-4) Reference Drop Delay Time Setting Step T4

In step T4, a control unit 71 sets a reference drop delay time.

(2-5) Positional Information Identifying Step T5

In step T5, the processing unit 73 identifies, as positional information, a luminance center position value calculated by maximum likelihood estimation from an image captured by the droplet camera 4.

(2-6) Imaging Controlling Step T6

In step T6, image information is acquired from the droplet camera 4 by sequentially changing, in increments of 0.1, the number of times and a reference droplet clock T sufficient to acquire correlation between the positional information and the light source lighting delay time, and the positional information is calculated.

(2-7) Correlation Equation Calculating Step T7

In step T7, the processing unit 73 calculates a correlation equation between the positional information and the light source lighting delay time on the basis of a plurality of different light source lighting delay times recorded in a recording unit 72 and positional information recorded in a manner correlated to each of the plurality of different light source lighting delay times.

(2-8) Drop Delay Time Determining Step T8

In step T8, the processing unit 73 determines, as a drop delay time, a light source lighting delay time identified on the basis of the target positional information and the correlation equation.

FIG. 11 provides views illustrating exemplary droplet images captured by the droplet camera 4 of a flow cytometer 1 and illustrates the images captured at different clock times (refer to FIGS. 11(a) to 11(d)). More specifically, FIG. 11 provides the views to describe in which number of droplet a detected fine particle is included in a case of defining, as a first droplet, a droplet D imaged by the droplet camera 4 at the time point t0 when the fine particle is detected by the detection unit 3. Meanwhile, each of the images can be the one in which a plurality of captured images is integrated.

In FIG. 11, the region D0 is a divided image region on the basis of a droplet image. The processing unit 73 compares images of a plurality of droplets D imaged at the interval of the droplet clock by the droplet camera 4 and determines, as a reference drop delay time, a temporary light source lighting delay time from the time point t0 until a clock time when the number of bright spots B becomes maximal in the region D0.

Figure 12:
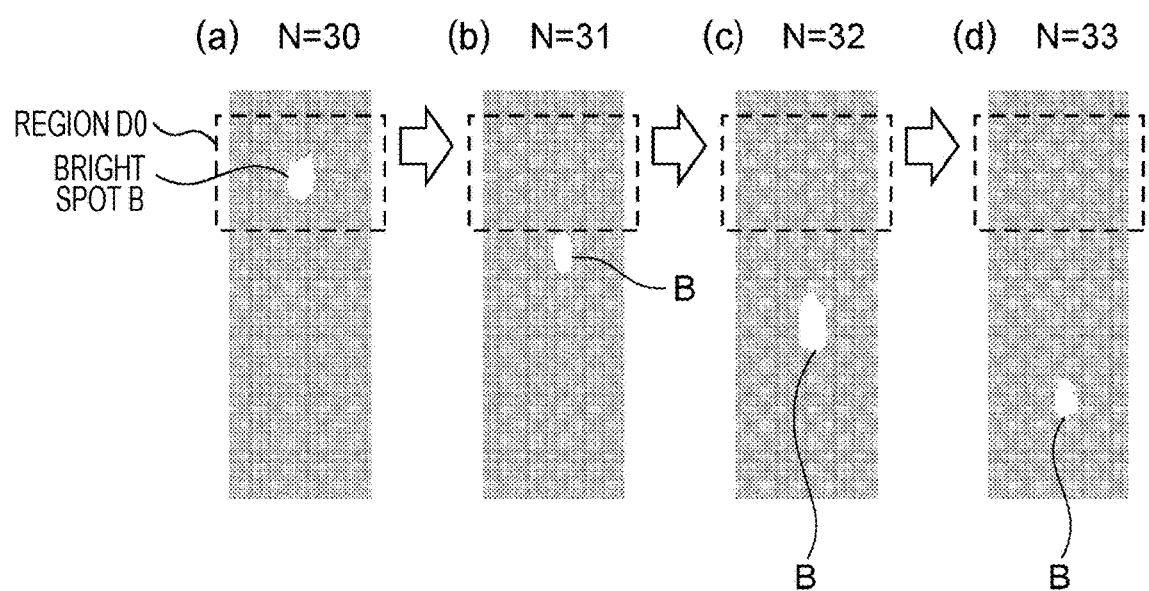
FIG. 12 provides views illustrating exemplary droplet images captured by a droplet camera 4 of the flow cytometer 1.

In FIG. 12, as the examples of the present disclosure, illustrated are the images captured by the droplet camera 4 when 30th to 33rd droplets are discharged in a case of defining, as a first droplet, a droplet D discharged from an orifice 21 and imaged by the droplet camera 4. For example, the 30th droplet is a diagram indicated as N=30 (refer to FIG. 12($a$)).

In the example illustrated in FIG. 12, the processing unit 73 can determine in the processing unit 73 that the 30th droplet includes a fine particle on the basis of image information of N=30 (refer to FIG. 12($a$)) in which the number of the bright spots B inside the region D0 is maximal. In other words, the processing unit 73 compares the plurality of images of the droplets D imaged at the interval of the droplet clock by the droplet camera 4 and determines, as the reference drop delay time, a temporary light source lighting delay time starting from the clock time when the fine particle is detected until a clock time when the 30th droplet is discharged.

Thus, in the image processing method according to the second embodiment of the present disclosure, the number of bright spots in image information inside the region D0 is compared between a plurality of different clock times, and the temporary light source lighting delay time can be determined as the reference drop delay time by executing coarse adjustment.

Furthermore, in the present disclosure, an image region is first divided into D0 to D2 on the basis of a droplet image, and the number of bright spots in the region D0 is acquired by sequentially changing the reference drop delay time in increments of 1, for example. Then, a time when the number of bright spots becomes maximal is to be a rough value of the drop delay time. In the subsequent fine adjustment step (T4 to T8), a drop delay time is changed into a shorter time by setting, for example, the droplet clock in increments of 0.1 on the basis of the reference drop delay time calculated in the above-described coarse adjustment step.

Thus, since the image processing method of the present disclosure includes two steps of the coarse adjustment step (steps T1 to T3) and the fine adjustment step (T4 to T8), the drop delay time can be calculated more accurately than in the case of executing only the coarse adjustment step (steps T1 to T3). Additionally, an adjustment interval is generally needed to be short in order to improve accuracy in an adjustment process, and this may increase an adjustment time, however; in the present method, the drop delay time is determined by calculating a correlation equation between the positional information of the fine particle and the light source lighting delay time in the fine adjustment step, and therefore, the drop delay time can be calculated with high accuracy in a short time.

Figure 13:
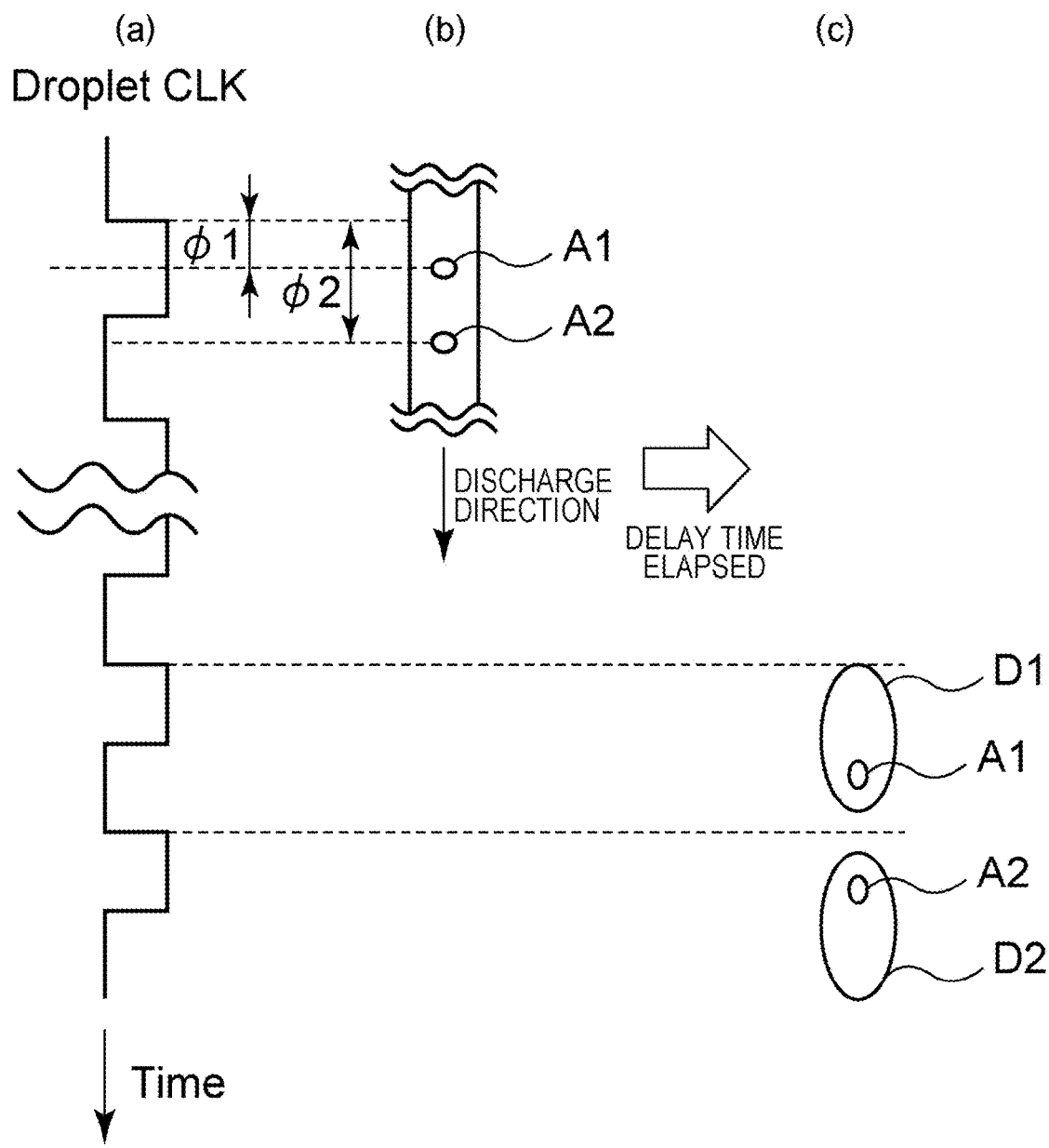
FIG. 13 provides schematic diagrams illustrating transition from when a fine particle is detected by a detection unit 3 until a droplet D including the fine particle is imaged by the droplet camera 4. (a) illustrates a graph of a droplet frequency (Droplet CLK), (b) illustrates fine particles detected by the detection unit and flowing through a flow path of a microchip, and (c) illustrates droplets including the fine particles respectively.

FIG. 13 provides schematic diagrams illustrating transition from when a fine particle is detected by the detection unit 3 until a droplet D including the fine particle is imaged by the droplet camera 4. FIG. 13($a$) illustrates a graph of a droplet frequency (Droplet CLK). Here, FIG. 13($b$) illustrates fine particles A1 and A2 flowing inside a flow path of a microchip 2 detected by the detection unit 3. Furthermore, in FIG. 13($c$), droplets D1 and D2 including the fine particles A1 and A2 respectively are illustrated.

In the example illustrated in FIG. 13, even in a case where the fine particles A1 and A2 are included in a same Droplet CLK, a phase is shifted by ($\varphi 2-\varphi 1$) (refer to FIG. 13($b$)). Therefore, the fine particles A1 and A2 may be included in the different droplets D1 and D2 respectively. In this case, timing to apply electric charge to a desired droplet may be different between the fine particles A1 and A2 (refer to FIG. 13($c$)). Therefore, it is necessary to adjust a drop delay time with high accuracy by using an interval shorter than the droplet clock in order to determine the timing to apply electric charge to a droplet with higher accuracy.

Meanwhile, the description has been described for the case where a fine particle flowing inside the flow path formed in the microchip is irradiated by the light source 31 (laser L1) and fluorescence or scattered light emitted from each fine particle is detected in the flow cytometer of the above embodiments, but the present invention is not limited thereto, and a fine particle flowing inside a flow path formed of a flow cell may be irradiated by the light source 31 (laser L1).

The image processing device, fine particle sorting device, and image processing method according to the present disclosure may also have the following configurations.

(1) An image processing device including:
    a control unit adapted to set a light source lighting delay time to control a light source, the light source lighting delay time indicating a time from a time point when a fine particle in fluid is detected by a detection unit until a time point when the light source is turned on for the fine particle included in a droplet formed from the fluid;
    a processing unit adapted to identify positional information of the fine particle on the basis of an image of the fine particle acquired in accordance with lighting of the light source during the set light source lighting delay time; and
    a recording unit adapted to record, in a correlated manner, the positional information identified in the processing unit and the light source lighting delay time,
    in which the processing unit determines, as a drop delay time, a light source lighting delay time correlated to target positional information that is predetermined positional information, and the drop delay time indicates a time from the time point when the fine particle is detected by the detection unit until the droplet is formed from the fluid containing the fine particle.

(2) The image processing device recited in (1) above, in which the positional information is identified on the basis of an image of a plurality of fine particles including the fine particle acquired during a predetermined time in which the light source lighting delay time is set.

(3) The image processing device recited in (2) above, in which the positional information is identified on the basis of luminance information acquired from the image of the plurality of fine particles.

(4) The image processing device recited in any one of (1) to (3) above, in which the processing unit calculates a correlation equation between the positional information and the light source lighting delay time on the basis of a plurality of different light source lighting delay times recorded in the recording unit and positional information recorded in a manner correlated to each of the plurality of different light source lighting delay times.

(5) The image processing device recited in (4) above, in which the processing unit determines, as a drop delay time, a light source lighting delay time identified on the basis of the target positional information and the correlation equation.

(6) The image processing device recited in (2) above, in which the positional information is calculated on the basis of a gravity center on a binary image generated from the acquired image of the plurality of fine particles.

(7) The image processing device recited in (2) above, in which the positional information is calculated by probability statistical processing on the basis of luminance information of the acquired image of the plurality of fine particles.

(8) The image processing device recited in any one of (1) to (7) above, in which the processing unit determines, as a reference drop delay time, a temporary light source lighting delay time indicating a time from a time point when one fine particle is detected by a detection unit out of a plurality of fine particles in the fluid until the one fine particle included in a droplet formed from the fluid comes to have a maximal number of bright spots in a reference region preset on an image captured by an imaging unit arranged in a downstream side of the detection unit, and the control unit controls the light source while setting the temporary light source lighting delay time as a time close to the reference drop delay time.

(9) The image processing device recited in any one of (1) to (8) above, in which the processing unit generates a binary image on the basis of the acquired image of the fine particle, and the control unit performs control so as to display the binary image on a display unit.

(10) The image processing device recited in any one of (1) to (9) above, in which the processing unit generates a plot diagram in which the positional information and the light source lighting delay time are set as variables on the basis of the plurality of different light source lighting delay times recorded in the recording unit and the positional information recorded in a manner correlated to each of the plurality of different light source lighting delay times, and the control unit performs control so as to display the plot diagram on a display unit.

(11) A fine particle sorting device including:

a detection unit adapted to detect a fine particle in fluid flowing inside a flow path;

a light source arranged in a downstream side of the detection unit;

a charging unit arranged in a downstream side of the light source and adapted to apply electric charge to a droplet including the fine particle included in the fluid;

a control unit adapted to set a light source lighting delay time to control the light source, the light source lighting delay time indicating a time from a time point when a fine particle in fluid is detected by the detection unit until a time point when the light source is turned on for the fine particle included in a droplet formed from the fluid;

a processing unit adapted to identify positional information of the fine particle on the basis of an image of the fine particle acquired in accordance with lighting of the light source during the set light source lighting delay time; and a recording unit adapted to record, in a correlated manner, the positional information identified in the processing unit and the light source lighting delay time, in which the processing unit determines, as a drop delay time, a light source lighting delay time correlated to target positional information that is predetermined positional information, and the drop delay time indicates a time from the time point when the fine particle is detected by the detection unit until the droplet is formed from the fluid containing the fine particle, and the control unit controls the charging unit so as to perform charging on the basis of the drop delay time determined by the processing unit.

(12) An image processing method including:

a controlling step of setting a light source lighting delay time and controlling a light source, the light source lighting delay time indicating a time from a time point when a fine particle in fluid is detected by a detection unit until a time point when the light source is turned on for the fine particle included in a droplet formed from the fluid;

a processing step of identifying positional information of the fine particle on the basis of an image of the fine particle acquired in accordance with lighting of the light source during the set light source lighting delay time; and a recording step of recording, in a correlated manner, the positional information identified in the processing step and the light source lighting delay time, in which, in the processing step, a light source lighting delay time correlated to target positional information that is predetermined positional information is determined as a drop delay time indicating a time from the time point when the fine particle is detected by the detection unit until the droplet is formed from the fluid containing the fine particle.

REFERENCE SIGNS LIST

1 Fine particle sorting device (flow cytometer)
11 Charging unit
12 Electrode
13 Vibration element
2 Microchip
2a Substrate layer
21 Orifice
22 Sample flow path
23 Sample inlet
24 Sheath inlet
25 Suction flow path
27 Straight portion
211 Cut-away portion
251 Suction outlet
252 Communication port
261, 262 Narrowed portion
3 Detection unit
31 Light source
4 Droplet camera
41 Light source
51, 52 Deflection plate
611, 612, 62, 63 Collection container
7 Image processing device
71 Control unit
72 Recording unit 73 Processing unit
B Bright spot
D Droplet
D0 to D2 Droplet region
S1 Reference drop delay time setting step
S2 Positional information identifying step
S3 Imaging controlling step
S4 Correlation equation calculating step
S5 Drop delay time determining step
T1 Temporary drop delay time determining step
T2 Step of acquiring number of bright spots
T3 Step of ranking number of bright spots
T4 Reference drop delay time setting step
T5 Positional information identifying step
T6 Imaging controlling step
T7 Correlation equation calculating step
T8 Drop delay time determining step

The invention claimed is:

1. An image processing device comprising:
a control unit configured to set a light source lighting delay time to control a light source, the light source lighting delay time indicating a time from a time point when a fine particle in fluid is detected by a detection unit until a time point when the light source is turned on for the fine particle included in a droplet formed from the fluid;
a processing unit configured to identify positional information of the fine particle on the basis of an image of the fine particle acquired in accordance with lighting of the light source during the set light source lighting delay time; and
a recording unit configured to record, in a correlated manner, the positional information identified in the processing unit and the light source lighting delay time,
wherein the processing unit determines, as a drop delay time, a light source lighting delay time correlated to target positional information that is predetermined positional information, and the drop delay time indicates a time from the time point when the fine particle is detected by the detection unit until the droplet is formed from the fluid containing the fine particle;
wherein the processing unit calculates a correlation equation between the positional information and the light source lighting delay time on the basis of a plurality of different light source lighting delay times recorded in the recording unit and positional information recorded in a manner correlated to each of the plurality of different light source lighting delay times.

2. The image processing device according to claim 1, wherein the positional information is identified on the basis of an image of a plurality of fine particles including the fine particle acquired during a predetermined time in which the light source lighting delay time is set.

3. The image processing device according to claim 2, wherein the positional information is identified on the basis of luminance information acquired from the image of the plurality of fine particles.

4. The image processing device according to claim 1, wherein the processing unit determines, as a drop delay time, a light source lighting delay time identified on the basis of the target positional information and the correlation equation.

5. The image processing device according to claim 2, wherein the positional information is calculated on the basis of a gravity center on a binary image generated from the acquired image of the plurality of fine particles.

6. The image processing device according to claim 2, wherein the positional information is calculated by probability statistical processing on the basis of luminance information of the acquired image of the plurality of fine particles.

7. The image processing device according to claim 1, wherein
the processing unit determines, as a reference drop delay time, a temporary light source lighting delay time indicating a time from a time point when one fine particle is detected by a detection unit out of a plurality of fine particles in the fluid until the one fine particle included in a droplet formed from the fluid comes to have a maximal number of bright spots in a reference region preset on an image captured by an imaging unit arranged in a downstream side of the detection unit, and
the control unit controls the light source while setting the temporary light source lighting delay time as a time close to the reference drop delay time.

8. The image processing device according to claim 1, wherein
the processing unit generates a binary image on the basis of the acquired image of the fine particle, and
the control unit performs control so as to display the binary image on a display unit.

9. The image processing device according to claim 1, wherein
the processing unit generates a plot diagram in which the positional information and the light source lighting delay time are set as variables on the basis of a plurality of different light source lighting delay times recorded in the recording unit and the positional information recorded in a manner correlated to each of the plurality of different light source lighting delay times, and
the control unit performs control so as to display the plot diagram on a display unit.

10. A fine particle sorting device comprising:
a detection unit configured to detect a fine particle in fluid flowing inside a flow path;
a light source arranged in upstream side of the detection unit;
a charging unit arranged in upstream side of the light source and configured to apply electric charge to a droplet including the fine particle included in the fluid;
a control unit configured to set a light source lighting delay time to control the light source, the light source lighting delay time indicating a time from a time point when a fine particle in fluid is detected by the detection unit until a time point when the light source is turned on for the fine particle included in a droplet formed from the fluid;
a processing unit configured to identify positional information of the fine particle on the basis of an image of the fine particle acquired in accordance with lighting of the light source during the set light source lighting delay time; and
a recording unit configured to record, in a correlated manner, the positional information identified in the processing unit and the light source lighting delay time,
wherein
the processing unit determines, as a drop delay time, a light source lighting delay time correlated to target positional information that is predetermined positional information, and the drop delay time indicates a time from the time point when the fine particle is detected by the detection unit until the droplet is formed from the fluid containing the fine particle, and the control unit controls the charging unit so as to perform charging on the basis of the drop delay time determined by the processing unit;

wherein the processing unit calculates a correlation equation between the positional information and the light source lighting delay time on the basis of a plurality of different light source lighting delay times recorded in the recording unit and positional information recorded in a manner correlated to each of the plurality of different light source lighting delay times.

11. An image processing method comprising:

a controlling step of setting a light source lighting delay time and controlling a light source, the light source lighting delay time indicating a time from a time point when a fine particle in fluid is detected by a detection unit until a time point when the light source is turned on for the fine particle included in a droplet formed from the fluid;

a processing step of identifying positional information of the fine particle on the basis of an image of the fine particle acquired in accordance with lighting of the light source during the set light source lighting delay time; and a recording step of recording, in a correlated manner, the positional information identified in the processing step and the light source lighting delay time, wherein, in the processing step, a light source lighting delay time correlated to target positional information that is predetermined positional information is determined as a drop delay time indicating a time from the time point when the fine particle is detected by the detection unit until the droplet is formed from the fluid containing the fine particle;

wherein the processing step calculates a correlation equation between the positional information and the light source lighting delay time on the basis of a plurality of different light source lighting delay times recorded in the recording unit and positional information recorded in a manner correlated to each of the plurality of different light source lighting delay times.

* * * * *